United States Patent
Anderson et al.

(12) 
(10) Patent No.: US 6,210,356 B1
(45) Date of Patent: *Apr. 3, 2001

(54) ULTRASOUND ASSEMBLY FOR USE WITH A CATHETER

(75) Inventors: James R. Anderson, Redmond; Gary Lichttenegger, Woodinville, both of WA (US)

(73) Assignee: Ekos Corporation, Bothell, WA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/129,980

(22) Filed: Aug. 5, 1998

(51) Int. Cl.[7] .................................................. A61B 17/20

(52) U.S. Cl. ............................................... 604/22; 601/2

(58) Field of Search ............................. 604/19–22, 93, 604/264; 601/1–2; 606/169–171, 27–8

(56) References Cited

U.S. PATENT DOCUMENTS

| | | | |
|---|---|---|---|
| 3,433,226 | 3/1969 | Boyd | 128/305 |
| 4,040,414 | 8/1977 | Suroff | 128/24 |
| 4,319,580 | 3/1982 | Colley et al. . | |
| 4,354,502 | 10/1982 | Colley et al. . | |
| 4,531,943 | 7/1985 | Van Tassel et al. . | |
| 4,729,384 | 3/1988 | Bazenet | 128/691 |
| 4,750,902 | 6/1988 | Wuchinich et al. | 604/22 |
| 4,780,212 | 10/1988 | Kost et al. . | |
| 4,781,677 | 11/1988 | Wilcox | 604/28 |
| 4,808,153 | 2/1989 | Parisi . | |
| 4,870,953 | 10/1989 | DonMichael et al. . | |
| 4,920,954 | 5/1990 | Alliger et al. . | |
| 4,924,863 | 5/1990 | Sterzer . | |
| 4,936,281 | 6/1990 | Stasz . | |
| 4,969,470 | 11/1990 | Mohl et al. | 128/673 |
| 5,021,044 | 6/1991 | Sharawy | 604/53 |
| 5,163,421 | 11/1992 | Bernstein et al. | 128/24.1 |
| 5,190,766 | 3/1993 | Ishihara | 424/489 |
| 5,197,946 | 3/1993 | Tachibana . | |
| 5,250,034 | 10/1993 | Appling et al. | 604/164 |
| 5,267,954 | 12/1993 | Nita . | |

(List continued on next page.)

FOREIGN PATENT DOCUMENTS

| | | | |
|---|---|---|---|
| 0 744 189 A1 | 11/1996 | (EP) | A61N/1/32 |
| WO 91/09629 | 7/1991 | (WO) | A61K/49/00 |
| WO 94/05361 | 3/1994 | (WO) | A61M/25/00 |
| WO 96/27341 | 9/1996 | (WO) | A61B/19/00 |
| WO 96/35469 | 11/1996 | (WO) | A61M/25/00 |
| WO 96/36286 | 11/1996 | (WO) | A61B/17/20 |
| WO 97/21462 | 6/1997 | (WO) | A61M/29/00 |

OTHER PUBLICATIONS

Hynynen et al.; "Small Cylindrical Ultrasound Sources For Induction of Hyperthermia Via Body Cavities or Interstitial Implants"; Arizona Cancer center and Department of Radiation Oncology, University of Arizona Health Sciences Center; vol. 9, No. 2, pp. 263–274; 1993.

Lee et al.; "Arrays of Multielement Ultrasound Applicators For Interstitial Hyperthermia"; *IEEE Transactions on Biomedical Engineering*; vol. 46, No. 7; Jul. 1999.

Primary Examiner—Angela D. Sykes
Assistant Examiner—Patricia Bianco
(74) Attorney, Agent, or Firm—Wilson Sonsini Goodrich & Rosati

(57) ABSTRACT

A catheter is disclosed. The catheter includes an elongated body with an exterior surface and an ultrasound transducer with a longitudinal length. A support member supports the ultrasound transducer at the exterior surface of the elongated body and defines a chamber adjacent to the exterior surface of the elongated body. The chamber reduces transmission of ultrasound energy from the ultrasound transducer into the elongated body along the longitudinal length of the ultrasound transducer.

40 Claims, 24 Drawing Sheets

U.S. PATENT DOCUMENTS

| | | | |
|---|---|---|---|
| 5,267,985 | 12/1993 | Shimada et al. | 604/290 |
| 5,269,291 | 12/1993 | Carter | 128/24 |
| 5,286,254 | 2/1994 | Shapland et al. | 604/21 |
| 5,295,484 | 3/1994 | Marcus et al. | 128/660.03 |
| 5,295,958 | 3/1994 | Shturman | 604/96 |
| 5,304,115 | 4/1994 | Pflueger et al. | 604/22 |
| 5,318,014 | 6/1994 | Carter | 601/2 |
| 5,323,769 | 6/1994 | Bommannan et al. | 601/2 |
| 5,327,891 | 7/1994 | Rammler | 128/658 |
| 5,328,470 | 7/1994 | Nabel et al. | 604/101 |
| 5,344,435 | 9/1994 | Turner et al. | 607/101 |
| 5,345,940 | 9/1994 | Seward et al. | 128/662.06 |
| 5,353,798 | 10/1994 | Sieben . | |
| 5,354,279 | 10/1994 | Hofling | 604/164 |
| 5,362,309 | 11/1994 | Carter | 604/22 |
| 5,363,853 | 11/1994 | Lieber et al. . | |
| 5,380,273 | 1/1995 | Dubrul et al. . | |
| 5,390,678 | 2/1995 | Gesswein et al. | 128/662.06 |
| 5,409,458 | 4/1995 | Khairkhahan et al. | 604/96 |
| 5,421,338 | 6/1995 | Crowley et al. | 128/662.06 |
| 5,423,797 | 6/1995 | Sorin et al. . | |
| 5,431,663 | 7/1995 | Carter | 604/128 |
| 5,445,155 | 8/1995 | Sieben . | |
| 5,447,509 | 9/1995 | Mills et al. | 606/1 |
| 5,458,568 | 10/1995 | Racchini et al. | 604/19 |
| 5,465,726 | 11/1995 | Dickinson et al. . | |
| 5,474,530 | 12/1995 | Passafaro et al. | 604/22 |
| 5,474,531 | 12/1995 | Carter | 604/22 |
| 5,498,238 | 3/1996 | Shapland et al. | 604/53 |
| 5,509,896 | 4/1996 | Carter | 604/21 |
| 5,514,092 | 5/1996 | Forman et al. . | |
| 5,520,189 | 5/1996 | Malinowski et al. | 128/662.03 |
| 5,603,327 | 2/1997 | Eberle et al. . | |
| 5,606,974 | 3/1997 | Castellano et al. . | |
| 5,617,851 | 4/1997 | Lipkovker | 128/632 |
| 5,618,275 | 4/1997 | Bock | 604/290 |
| 5,620,479 * | 4/1997 | Diederich | 607/97 |
| 5,628,730 | 5/1997 | Shapland | 604/21 |
| 5,660,180 | 8/1997 | Malinowski et al. | 128/660.03 |
| 5,695,460 | 12/1997 | Siegal et al. | 604/21 |
| 5,725,494 | 3/1998 | Brisken | 604/22 |
| 5,735,811 | 4/1998 | Brisken | 604/22 |
| 5,770,222 | 6/1998 | Unger et al. | 424/450 |

* cited by examiner

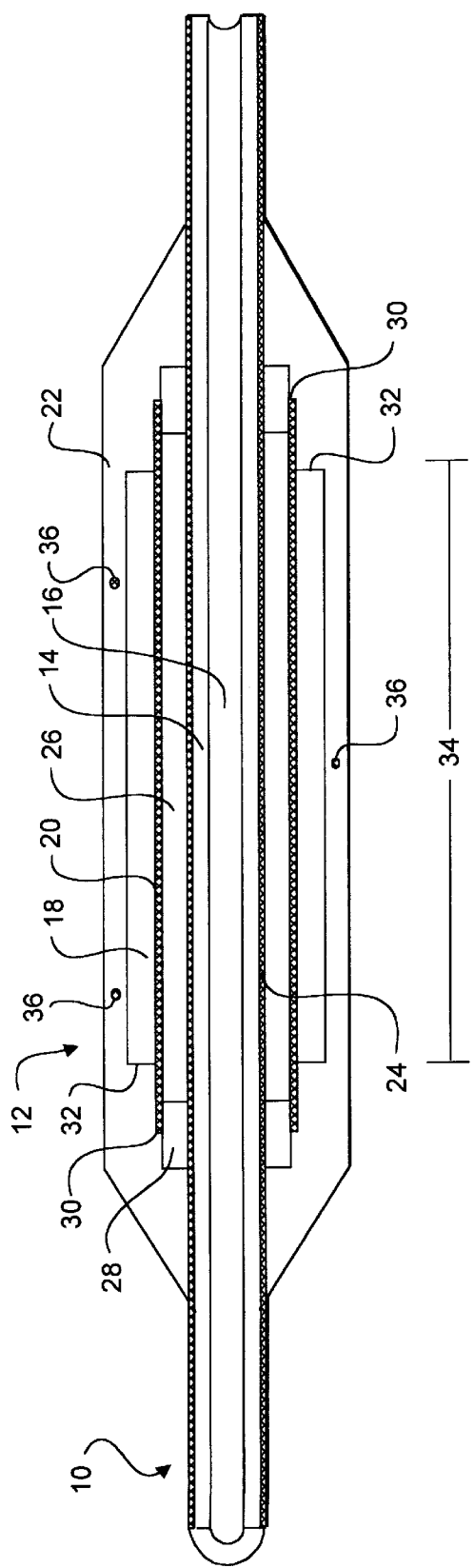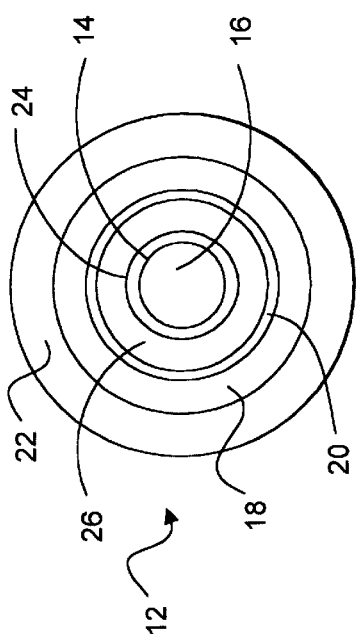
FIG. 1A
FIG. 1B

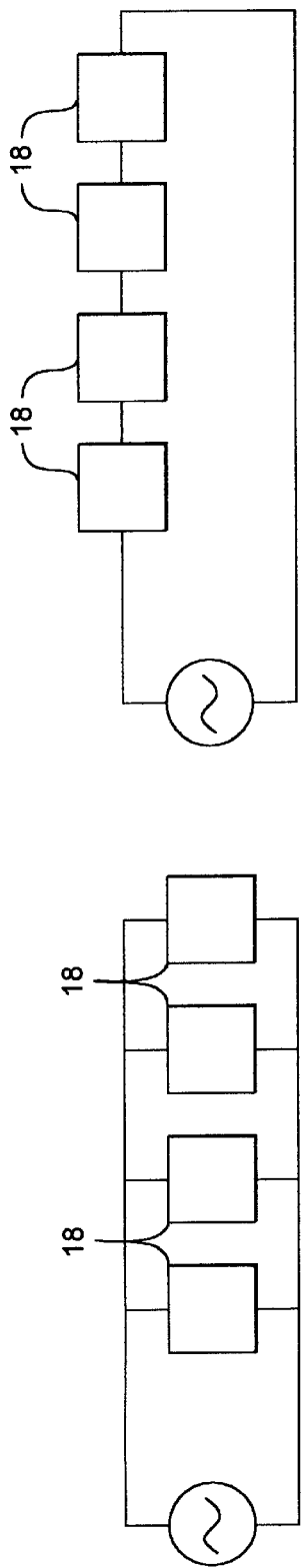
FIG. 9B
FIG. 9A
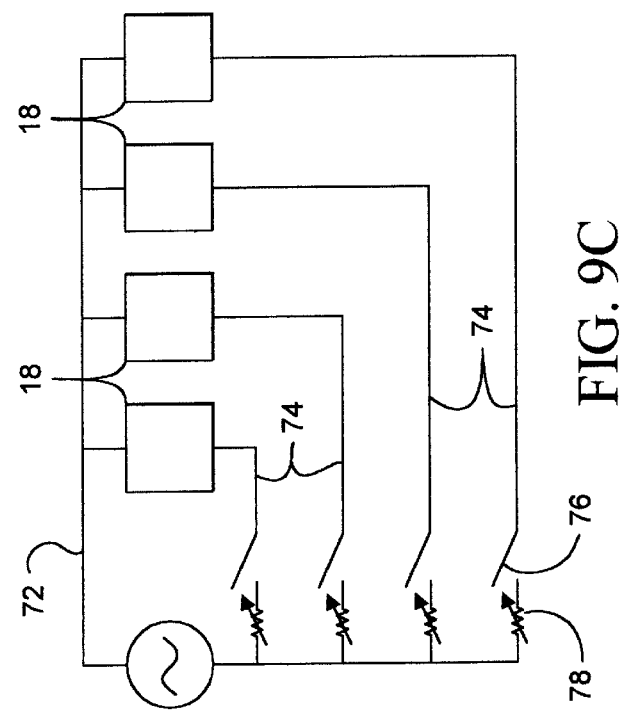
FIG. 9C

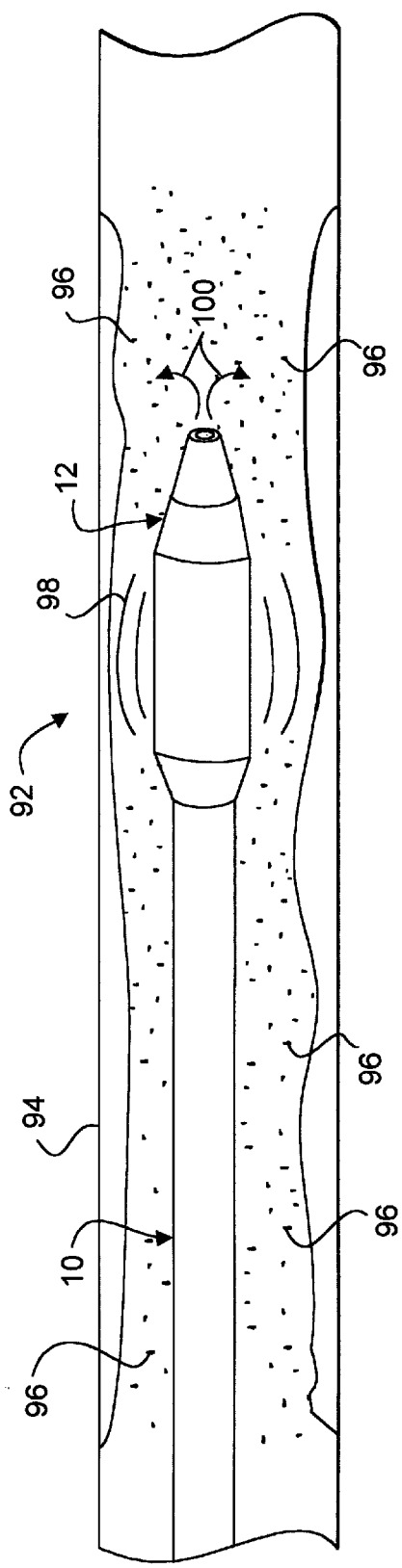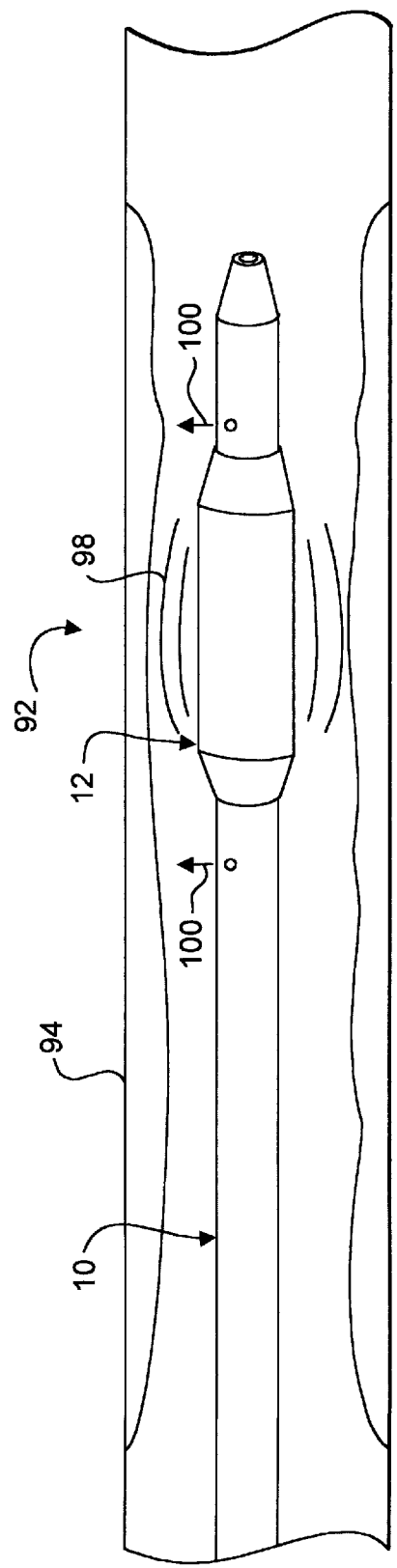

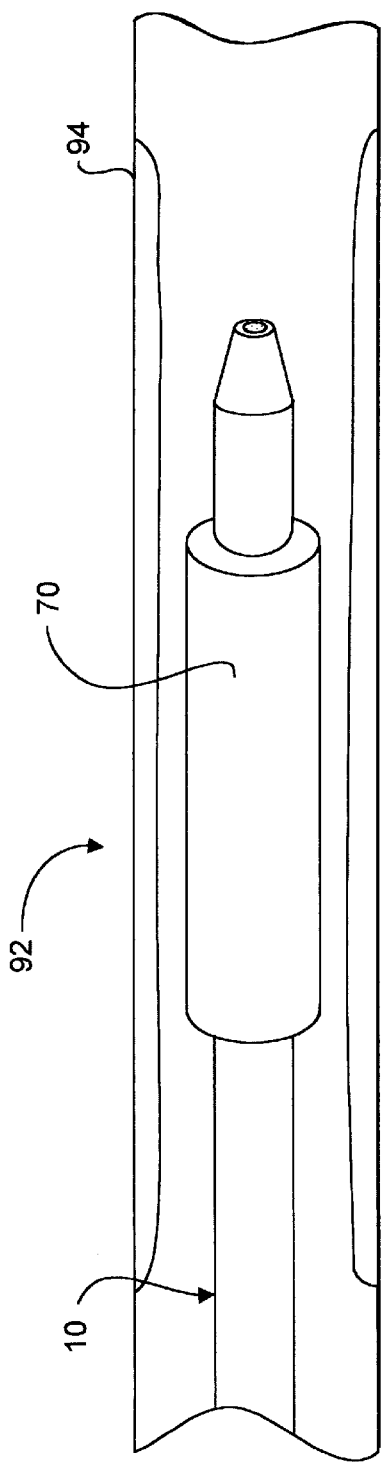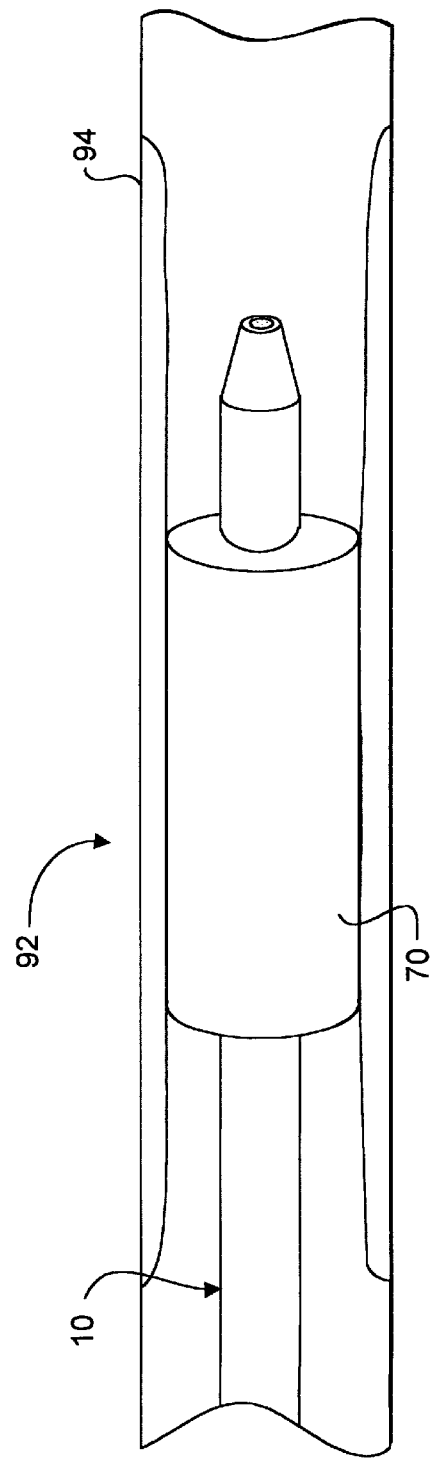
FIG. 12D
FIG. 12E

ULTRASOUND ASSEMBLY FOR USE WITH A CATHETER

BACKGROUND OF THE INVENTION

1. Field of the Invention

The present invention relates to a catheter with an ultrasound assembly, and more particularly, to a catheter with an ultrasound assembly which reduces the exposure of at least one lumen within the catheter to ultrasound energy.

2. Description of Related Art

It is frequently desirable to use a catheter to deliver various media to treatment sites within the body. The delivered media frequently includes drugs, medicaments, microbubbles and other therapeutically beneficial compounds. For instance, catheters are frequently used to treat thrombi which have formed in the cardiovascular vessels of the body. These catheters are used to deliver solutions containing dissolution compounds directly to the thrombus. Many catheters include an ultrasound transducer for delivering ultrasound energy to media which has been delivered to the treatment site. The ultrasound energy in combination with the delivered media and/or the ultrasound energy can enhance the desired therapeutic effects.

The media are typically delivered to the treatment site through lumens in the catheter. These lumens frequently must pass near the ultrasound transducer. As a result, the media can be exposed to the ultrasound energy before the media is delivered to the treatment site. This exposure can reduce the therapeutic effect of the media. For instance, when the delivered media is microbubbles, the microbubbles can be burst within the lumen before the microbubbles are delivered. The therapeutic effect from microbubbles can be a result of the microbubbles bursting after delivery to the treatment site. Bursting the microbubbles before they are delivered to the treatment site can deprive the treatment site of this therapeutic effect.

Many catheters suitable for the delivery of media and microbubbles are frequently positioned within a patient using over he-guidewire placement techniques. When these techniques are used, it is frequently desirable to leave the guidewire within a catheter during the delivery of the media and the ultrasound energy. However, the presence of the guidewire within the catheter can alter the frequency of the ultrasound energy produced by the ultrasound transducer. As a result, the frequency of the ultrasound energy actually produced by the ultrasound transducer may be different than the desired frequency.

There is a need for a catheter including an ultrasound assembly which reduces the exposure of lumens within the catheter to ultrasound energy delivered from the ultrasound transducer.

SUMMARY OF THE INVENTION

An object for an embodiment of the invention is providing a catheter for delivering ultrasound energy to a treatment site within a vessel.

Another object for an embodiment of the invention is providing a catheter for delivering ultrasound energy and another media to a treatment site within a vessel.

Yet another object for an embodiment of the invention is providing a catheter for delivering ultrasound energy and media to a treatment site within a vessel while reducing the exposure of the media to the ultrasound energy while the media is transported through the catheter.

Yet another object for an embodiment of the invention is providing a catheter for delivering ultrasound energy to a treatment site within a vessel while reducing the effects of a guidewire positioned in a lumen of the catheter on the frequency of the ultrasound energy.

A further object for an embodiment of the invention is providing a catheter including an ultrasound transducer adjacent to a chamber which extends along the longitudinal length of the ultrasound transducer.

Yet further object for an embodiment of the invention is providing a catheter including an ultrasound transducer adjacent to a chamber which extends along the longitudinal length of the ultrasound transducer and is filled with a low acoustic impedance material.

An even further object for an embodiment of the invention is providing a catheter including an ultrasound transducer adjacent to an evacuated chamber which extends along the longitudinal length of the ultrasound transducer.

A catheter is disclosed. The catheter includes an elongated body with an exterior surface and an ultrasound transducer with a longitudinal length. A support member supports the ultrasound transducer at the exterior surface of the elongated body and defines a chamber adjacent to the exterior surface of the elongated body. The chamber reduces transmission of ultrasound energy from the ultrasound transducer into the elongated body along the longitudinal length of the ultrasound transducer.

Another embodiment of the catheter includes an elongated body with an exterior surface and an ultrasound transducer with a longitudinal length. A support member supports the ultrasound transducer at the exterior surface of the elongated body. The support member at least partially defines a chamber adjacent to the exterior surface of the elongated body. The chamber extends continuously along the longitudinal length of the ultrasound transducer.

Another embodiment of the catheter includes an elongated body with an exterior surface and at least partially defining a chamber adjacent to the exterior surface of the elongated body. An ultrasound transducer is positioned adjacent the chamber and a coating is adjacent an external surface of the ultrasound transducer. At least one temperature sensor is coupled with the coating.

Another embodiment of the catheter includes an elongated body defining at least a portion of a chamber and an ultrasound transducer positioned on an opposite side of the chamber from the elongated body. A balloon is coupled with the elongated body.

An ultrasound assembly for use with a catheter is also disclosed. The assembly includes an elongated body with an exterior surface and an ultrasound transducer with a longitudinal length. A support member supports the ultrasound transducer at the exterior surface of the elongated body and at least partially defines a chamber adjacent to the exterior surface of the elongated body. At least one assembly end is configured to be coupled with the catheter.

Another embodiment of the ultrasound assembly includes an elongated body with an exterior surface and an ultrasound transducer with a longitudinal length. A support member supports the ultrasound transducer at the exterior surface of the elongated body and at least partially defines a chamber adjacent to the exterior surface of the elongated body. The chamber extends continuously along the longitudinal length of the ultrasound transducer.

Yet another embodiment of the ultrasound assembly includes an elongated body defining at least a portion of a chamber and an ultrasound transducer positioned on an opposite side of the chamber from the elongated body. At least one assembly end is configured to be coupled with the catheter.

BRIEF DESCRIPTION OF THE FIGURES

FIG. 1A is a cross section of an ultrasound assembly according to the present invention.

FIG. 1B is a cross section of an ultrasound assembly according to the present invention.

FIG. 9A illustrates ultrasound transducers connected in parallel.

FIG. 9B illustrates ultrasound transducers connected in series.

FIG. 9C illustrates ultrasound transducers connected with a common line.

FIG. 12A illustrates an ultrasound assembly positioned adjacent a treatment site and microbubbles delivered via a utility lumen.

FIG. 12B illustrates an ultrasound assembly positioned adjacent a treatment site and a media delivered via a media delivery port.

FIG. 12D illustrates a catheter including a balloon positioned adjacent a treatment site.

FIG. 12E illustrates a catheter including a balloon expanded into contact with a treatment site.

DETAILED DESCRIPTION

Figure 1C:
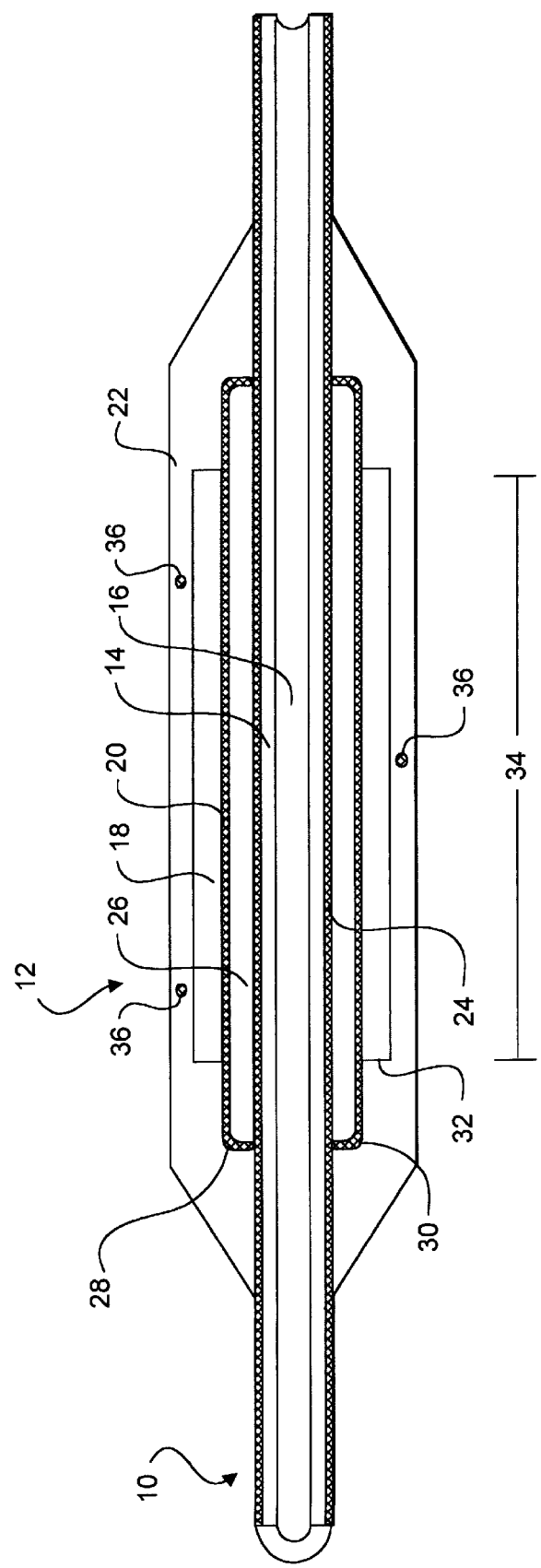
FIG. 1C illustrates a support member with integral supports.

The present invention relates to a catheter including an ultrasound assembly. The catheter includes an elongated body with at least one utility lumen extending through the elongated body. The utility lumens can be used to deliver various media to a treatment site and/or to receive a guidewire so the catheter can be guided to the treatment site. The ultrasound assembly can include an ultrasound transducer which can transmit ultrasound energy. A support member can support the ultrasound transducer adjacent an outer surface of the elongated body so as to define a chamber between the ultrasound transducer and the elongated body.

The chamber can be filled with a material which creates a low acoustic impedance to reduce the exposure of at least one utility lumen within the elongated body to ultrasound energy delivered from the ultrasound transducer. For instance, the chamber can be filled with a material which absorbs, reflects or prevents transmission of ultrasound energy through the chamber. Alternatively, the chamber can be evacuated to reduce transmission of ultrasound energy through the chamber.

The support member can have ends which extend beyond the ultrasound member. As a result, the chamber can be positioned adjacent the entire longitudinal length of the ultrasound transducer and can extend beyond the ends of the ultrasound transducer. This configuration maximizes the portion of the ultrasound transducer which is adjacent the chamber. Increasing the portion of ultrasound transducer adjacent to the chamber can reduce the amount of ultrasound energy transmitted to the utility lumens. The ultrasound assembly can include an outer coating over the ultrasound transducer. Temperature sensors can be positioned in the outer coating adjacent to ultrasound transducer. This position of the temperature sensors feedback regarding the temperature adjacent to the ultrasound transducers where the thermal energy has a reduced opportunity to dissipate. As a result, the temperature sensors provide a measure of the temperature on the exterior surface of the transducer.

FIGS. 1A–1B illustrates a catheter 10 including an ultrasound assembly 12 according to the present invention. The catheter 10 includes an elongated body 14 with a utility lumen 16 extending through the elongated body 14. The utility lumen 16 can receive a guidewire so the catheter 10 can be threaded along the guidewire. The utility lumen 16 can also be used for the delivery of media which includes drugs, medication, microbubbles and other compounds which provide a therapeutic effect.

The ultrasound assembly 12 includes an ultrasound transducer 18. Suitable ultrasound transducers 18 include, but are not limited to, PZT-4D, PZT-4, PZT-8 and cylindrically shaped piezoceramics. When the ultrasound transducer 18 has a cylindrical shape, the ultrasound transducer 18 can encircle the elongated body 14 as illustrated in FIG. 1B. The ultrasound assembly 12 also includes a support member 20. Suitable support members 20 include, but are not limited to, polyimide, polyester and nylon. The support member 20 can be attached to the ultrasound transducer 18. Suitable means for attaching the ultrasound transducer 18 to the support member 20 include, but are not limited to, adhesive bonding and thermal bonding. The ultrasound assembly 12 can also include an outer coating 22.

Suitable outer coatings 22 include, but are not limited to, polyimide, parylene and polyester.

Figure 1D:
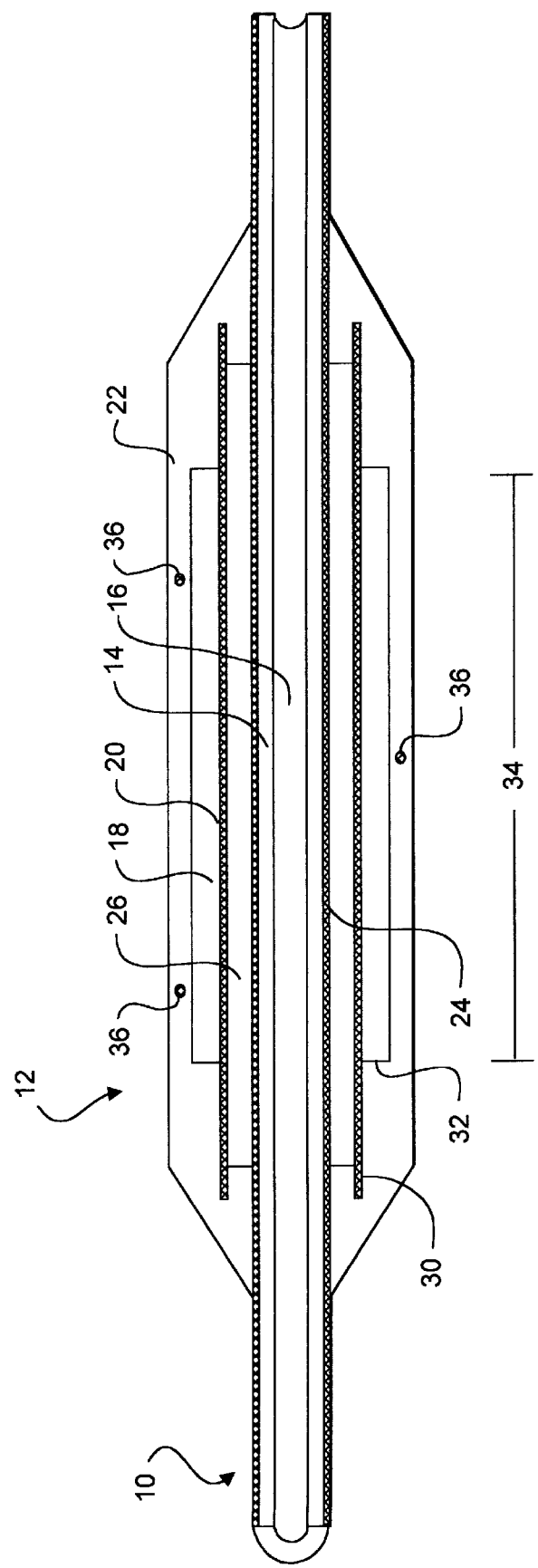
FIG. 1D illustrates a support member which is supported by an outer coating.

The support member 20 supports the ultrasound member 20 at an external surface 24 of the elongated body 14 such that a chamber 26 is defined between the ultrasound transducer 18 and the external surface 24 of the elongated body 14. The chamber 26 preferably has a height from 0.25–10 $\mu$m, more preferably from 0.50–5 $\mu$m and most preferably from 0.0–1.5 $\mu$m. The support member 20 can be supported by supports 28 positioned at the ends 30 of the support member 20 as illustrated in FIG. 1A. The supports 28 can be integral with the support member 20 as illustrated in FIG. 1C. The outer coating 22 can serve as the supports as illustrated in FIG. 1D.

The ends 30 of the support member 20 can extend beyond the ends 32 of the ultrasound transducer 18. The supports 28 can be positioned beyond the ends 32 of the ultrasound transducer 18. As a result, the chamber 26 can extend along the longitudinal length 34 of the ultrasound transducer 18, maximizing the portion of the ultrasound transducer 18 which is adjacent to the chamber 26. The chamber 26 can be filled with a medium which absorbs ultrasound energy or which prevents transmission of ultrasound energy. Suitable gaseous media for filling the chamber 26 include, but are not limited to, helium, argon, air and nitrogen. Suitable solid media for filling the chamber 26 include, but are not limited to, silicon and rubber. The chamber 26 can also be evacuated. Suitable pressures for an evacuated chamber 26 include, but are not limited to, negative pressures to –760 mm Hg.

One or more temperature sensors 36 can be positioned in the outer coating 22. The temperature sensors 36 can be positioned adjacent the ultrasound transducer 18 to provide feedback regarding the temperature adjacent the ultrasound transducer 18.

Figure 2A:
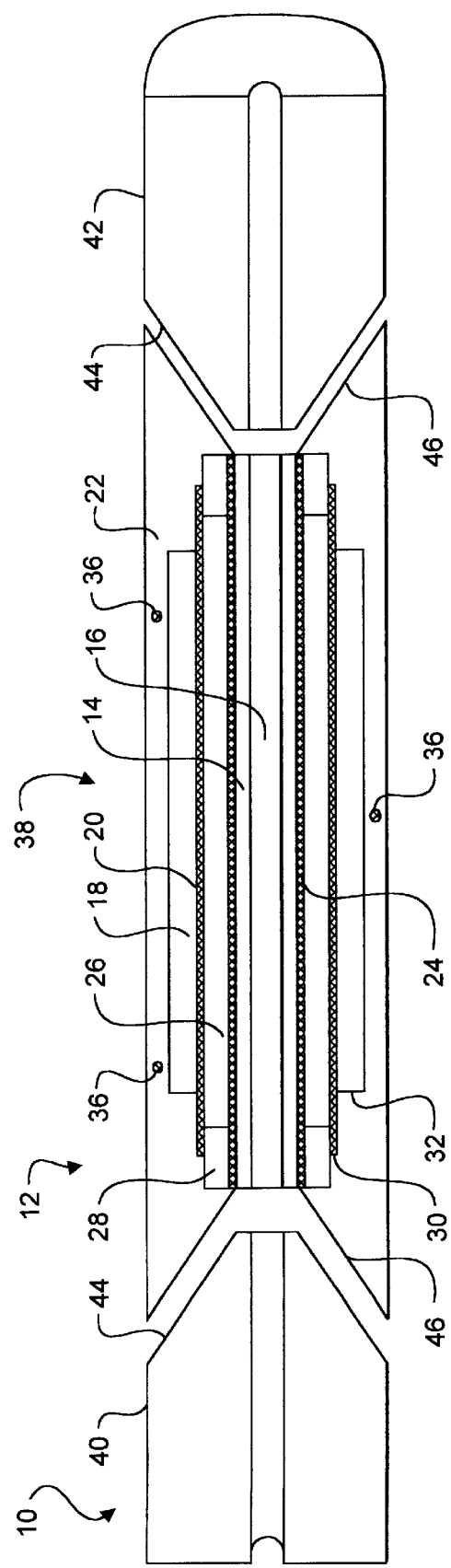
FIG. 2A is a cross section of a catheter which includes an ultrasound assembly module which is independent of a first catheter component and a second catheter component.
Figure 2B:
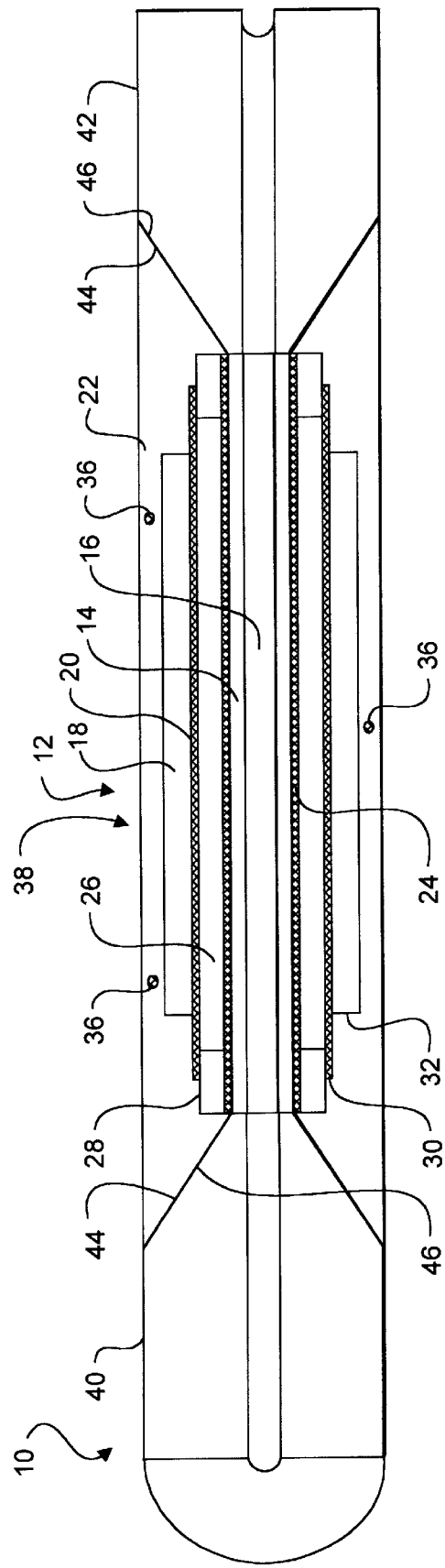
FIG. 2B illustrates the first and second catheter components coupled with the ultrasound assembly module.
Figure 2C:
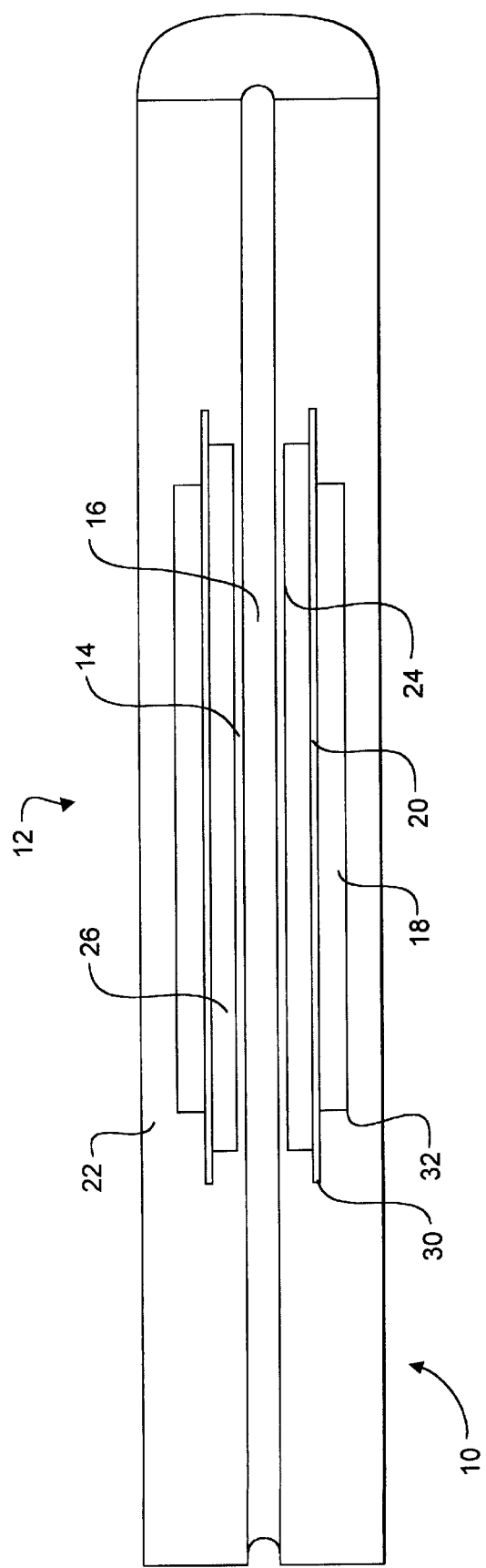
FIG. 2C is a cross section of an ultrasound assembly which is integral with a catheter.

The ultrasound assembly 12 can be a separate module 38 as illustrated in FIGS. 2A–2B. In FIG. 2A, the catheter 10 includes a first catheter component 40 a second catheter component 42 and an ultrasound assembly module 38. The first and second catheter components 40, 42 include component ends 44 which are complementary to the ultrasound assembly module ends 46. The component ends 44 can be coupled with the ultrasound assembly module ends 46 as illustrated in FIG. 2B. Suitable means for coupling the component ends 44 and the ultrasound assembly module ends 46 include, but are not limited to, adhesive, mechanical and thermal methods. The ultrasound assembly 12 can be integral with the catheter 10 as illustrated in FIG. 2C. Further, the outer coating 22 can have a diameter which is larger than the diameter of the elongated body 14 as illustrated in FIG. 1A or can be flush with the external surface 24 of the elongated body 14 as illustrated in FIGS. 2A–2C.

Figure 3A:
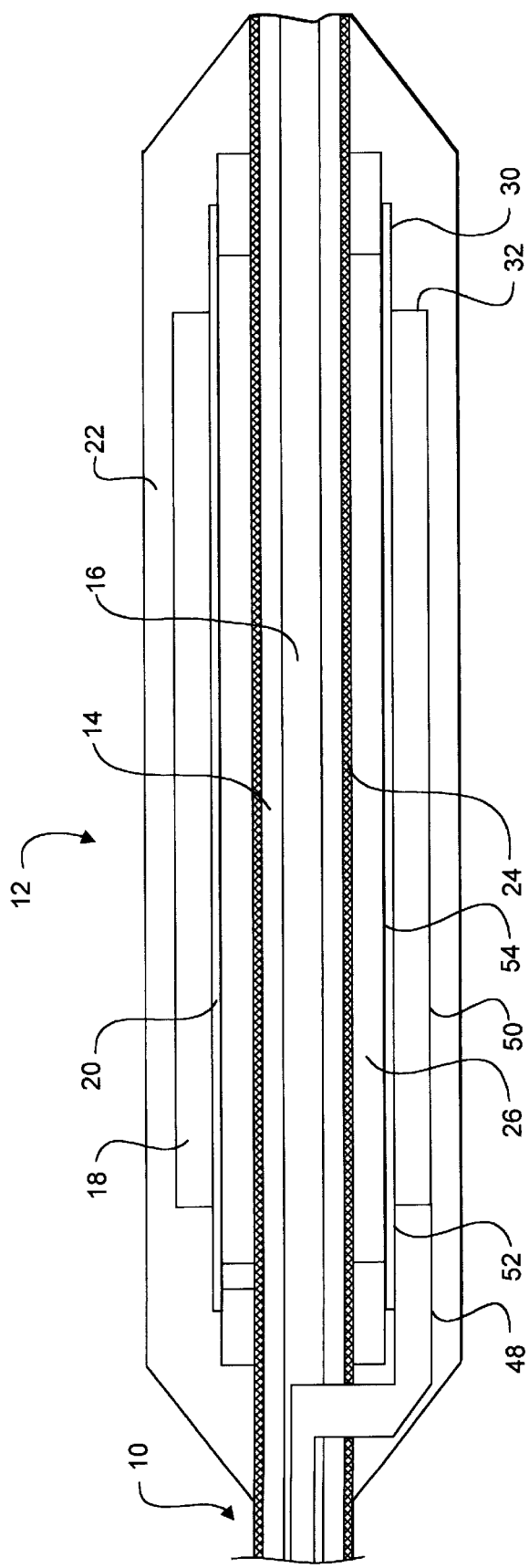
FIG. 3A is a cross section of an ultrasound assembly configured to radiate ultrasound energy in a radial direction. The wires which drive the ultrasound transducer pass through a utility lumen in the catheter.
Figure 3B:
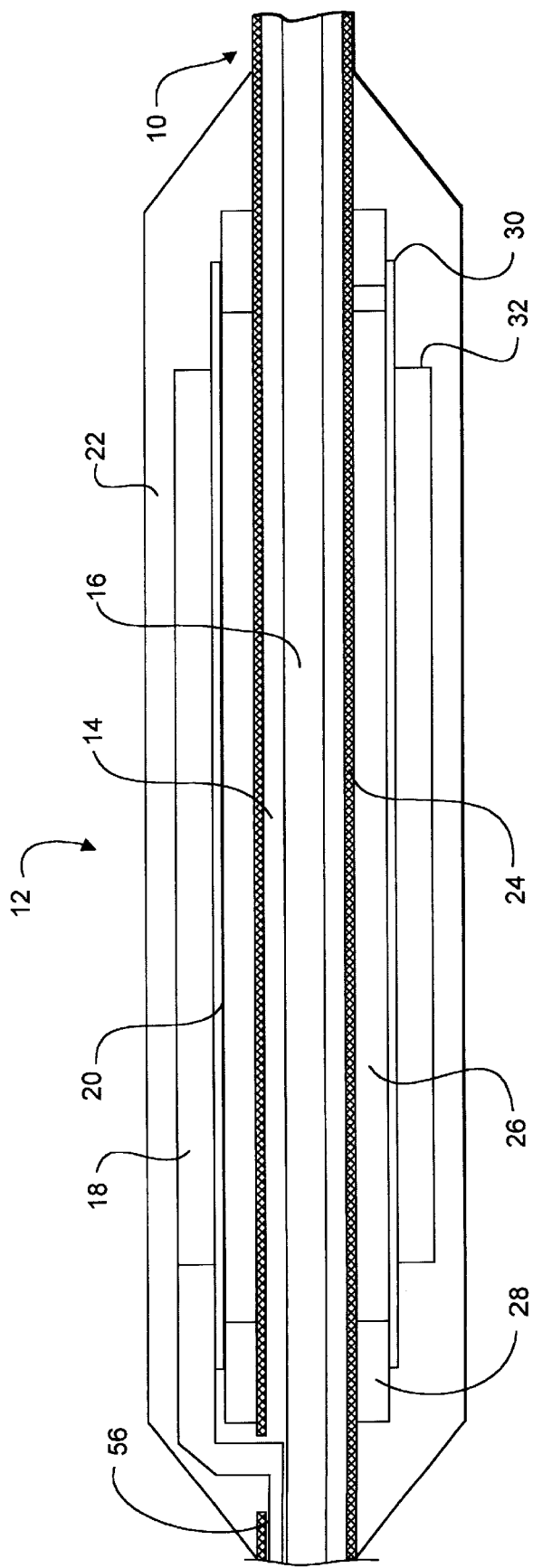
FIG. 3B is a cross section of an ultrasound assembly configured to radiate ultrasound energy in a radial direction. The lines which drive the ultrasound transducer pass through line lumens in the catheter.

The ultrasound assembly 12 can be electrically coupled to produce radial vibrations of the ultrasound transducer 18 as illustrated in FIGS. 3A–3B. A first line 48 is coupled with an outer surface 50 of the ultrasound transducer 18 while a second line 52 is coupled with an inner surface 54 of the ultrasound transducer 18. The first and second lines 48, 52 can pass proximally through the utility lumen 16 as illustrated in FIG. 3A. Alternatively, the first and second lines 48, 52 can pass proximally through line lumens 56 within the catheter 10 as illustrated in FIG. 3B. Suitable lines for the ultrasound transducer 18 include, but are not limited to, copper, gold and aluminum. Suitable frequencies for the ultrasound energy delivered by the ultrasound transducer 18 include, but are not limited to, 20 KHz to 2 MHz.

Figure 3C:
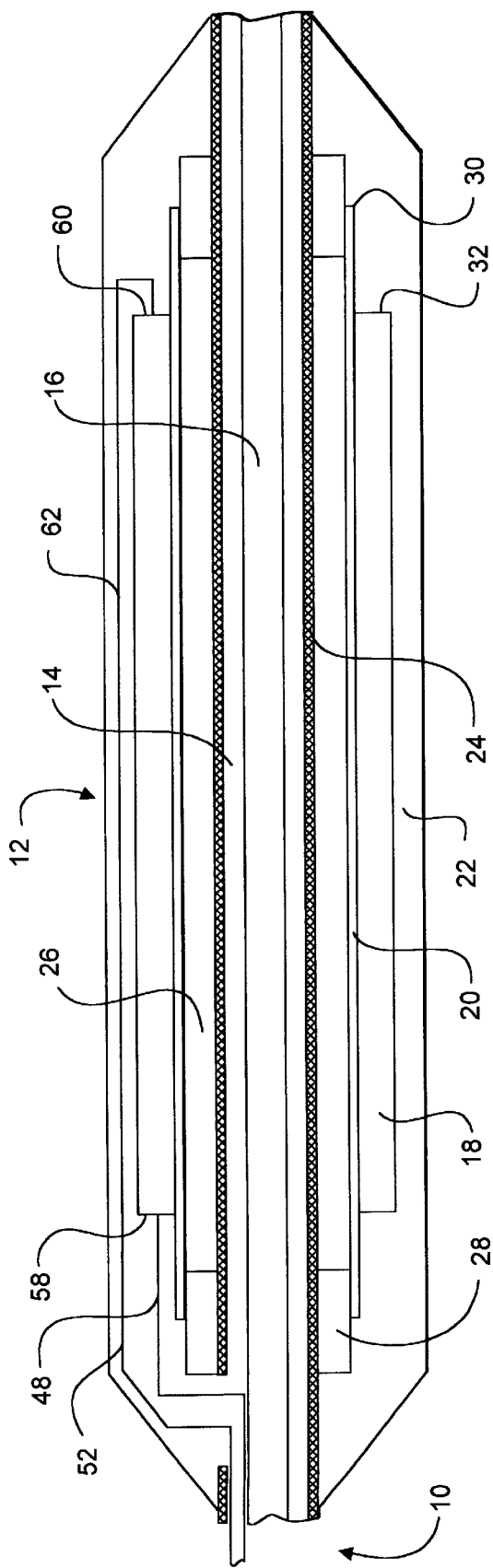
FIG. 3C is a cross section of an ultrasound assembly configured to longitudinally radiate ultrasound energy. The distal portion of one line travels proximally through the outer coating.
Figure 3D:
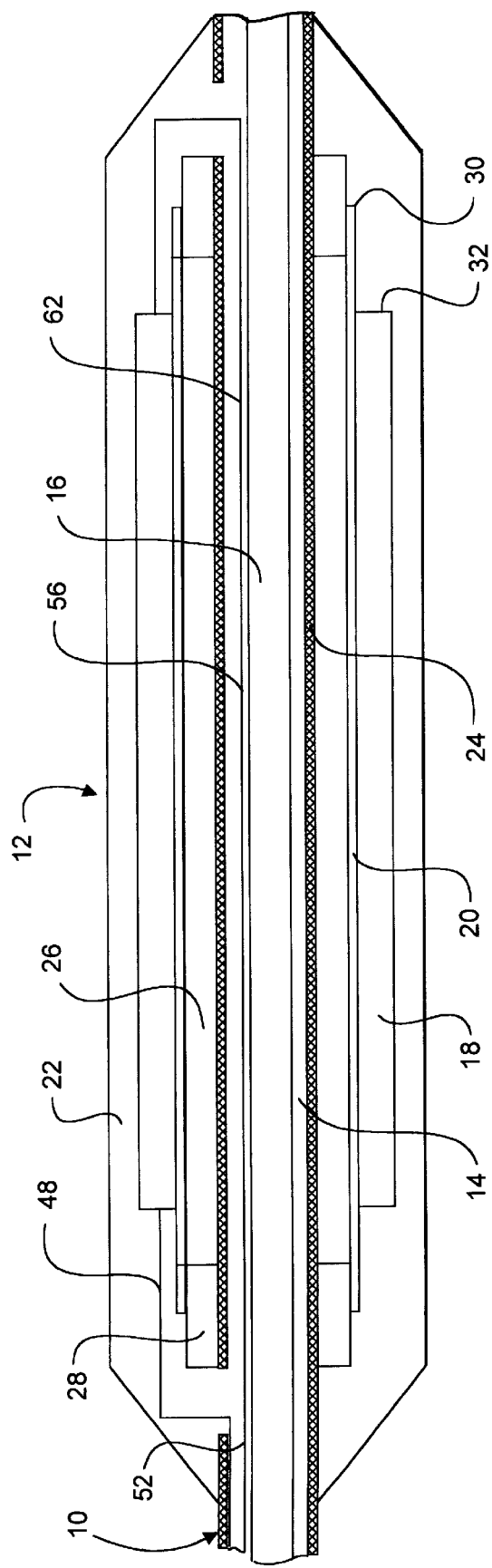
FIG. 3D is a cross section of an ultrasound assembly configured to longitudinally transmit ultrasound energy. The distal portion of one line travels proximally through a line lumen in the catheter.

The ultrasound assembly 12 can be electrically coupled to produce longitudinal vibrations of the ultrasound transducer 18 as illustrated in FIGS. 3C–3D. A first line 48 is coupled with a first end 58 of the ultrasound transducer 18 while a second line 52 is coupled with a second end 60 of the ultrasound transducer 18. The distal portion 62 of the second line 52 can pass through the outer coating 22 as illustrated in FIG. 3C. Alternatively, the distal portion 62 of the second line 52 can pass through line lumens 56 in the catheter 10 as illustrated in FIG. 3D. As discussed above, the first and second lines 48, 52 can pass proximally through the utility lumen 16.

Figure 4A:
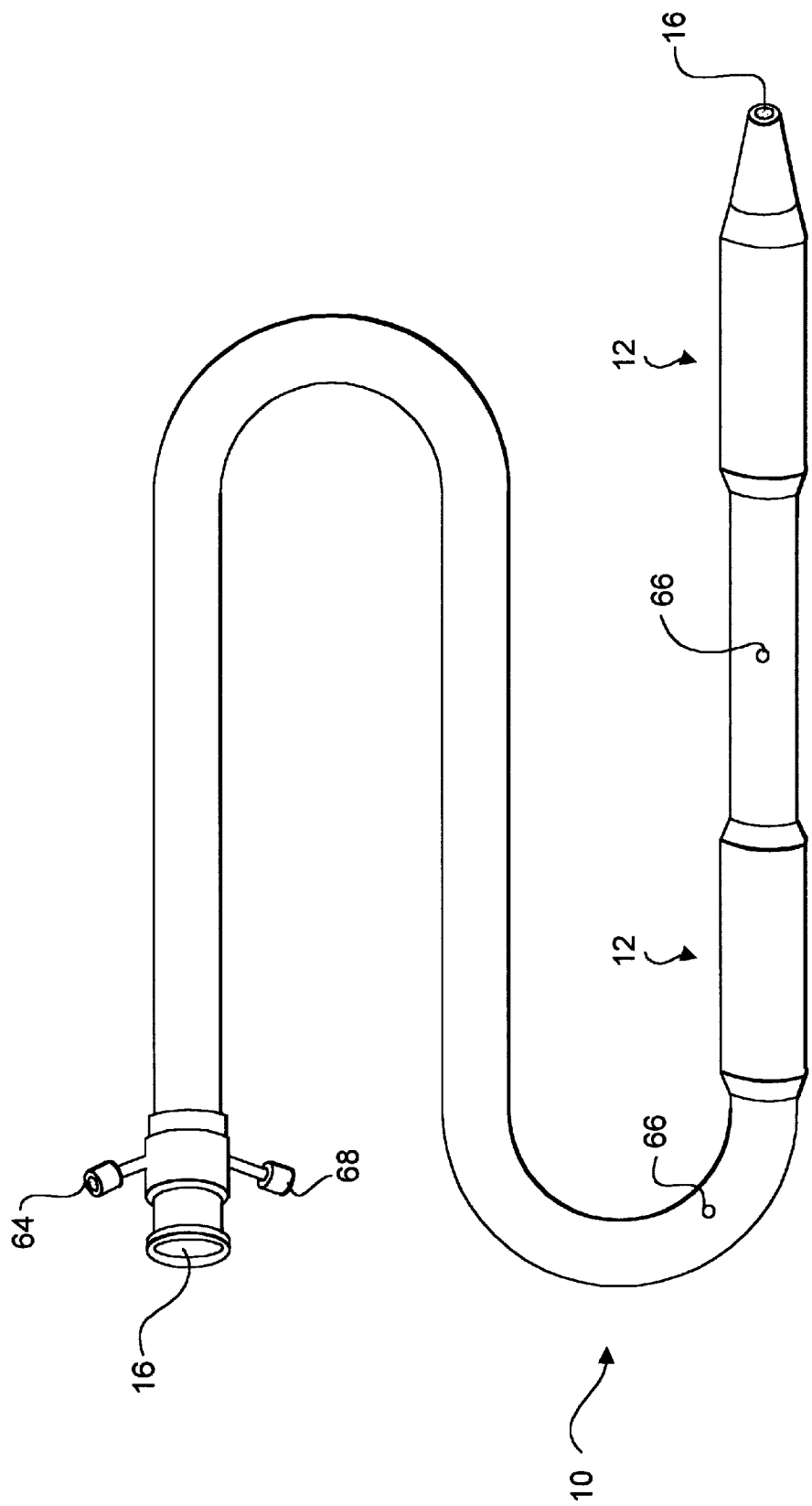
FIG. 4A is a sideview of a catheter including a plurality of ultrasound assemblies.
Figure 4C:
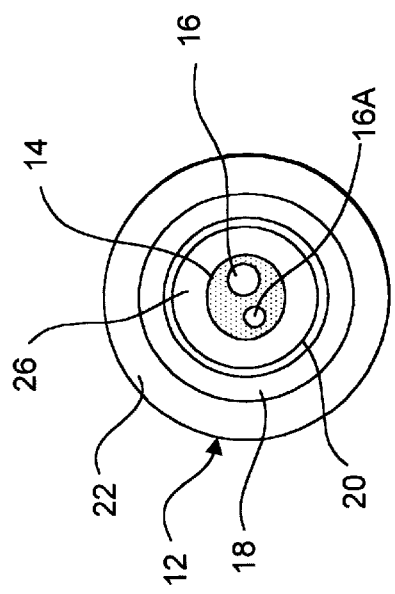
FIG. 4C is a cross section of an ultrasound assembly included on a catheter with a plurality of utility lumens.
Figure 4B:
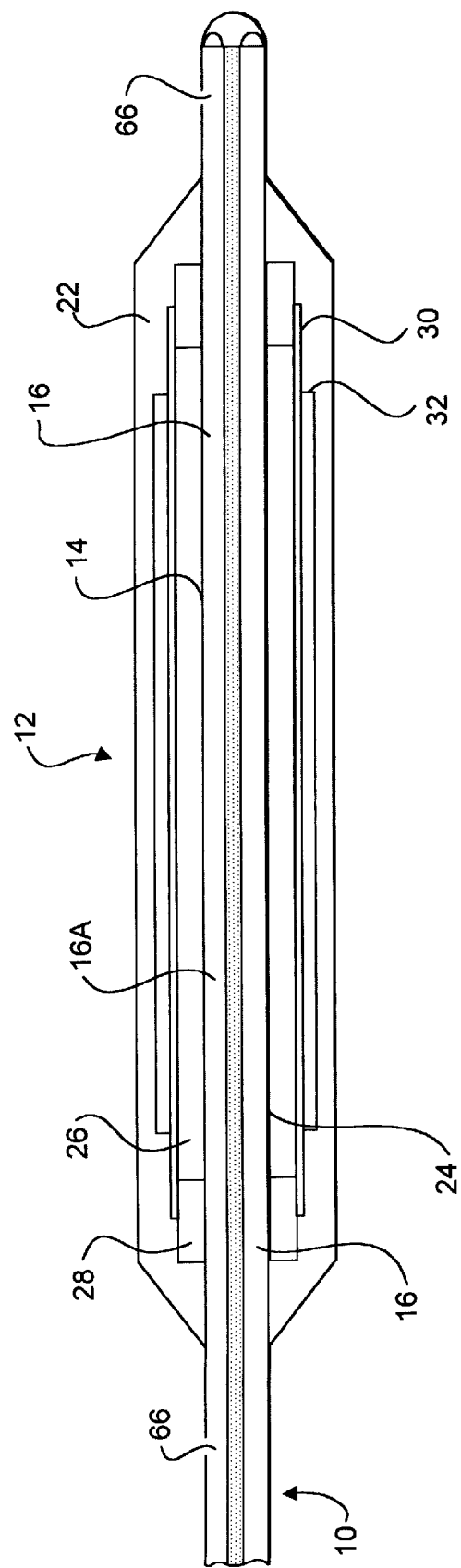
FIG. 4B is a cross section of an ultrasound assembly included on a catheter with a plurality of utility lumens.

FIG. 4A illustrates a catheter 10 including a plurality of ultrasound assemblies. The catheter 10 includes an electronics coupling 64, a plurality of media delivery ports 66 and a media inlet port 68. The electronics coupling 64 is designed to be coupled with electronics (not shown) which receive signals from the temperature sensors 36. FIGS. 4B–4C are cross sections of a catheter 10 with a second utility lumen 16A coupled with the media delivery ports 66. The second utility lumen 16A can also be coupled with the media inlet port 68 illustrated in FIG. 4A. The media inlet port 68 is designed to be coupled with a media source (not shown). Media can be transported from the media source and through the media delivery ports 66 via the second utility lumen 16A.

Figure 5A:
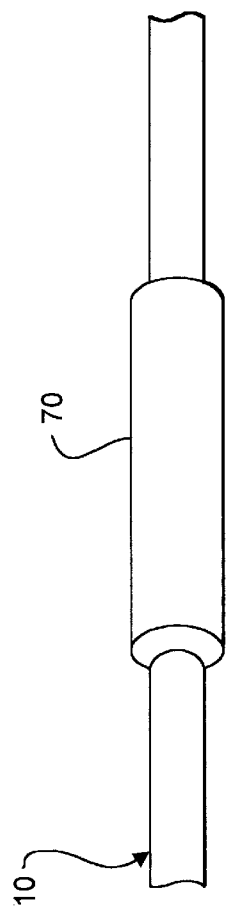
FIG. 5A is a sideview of a catheter including a balloon.
Figure 5B:
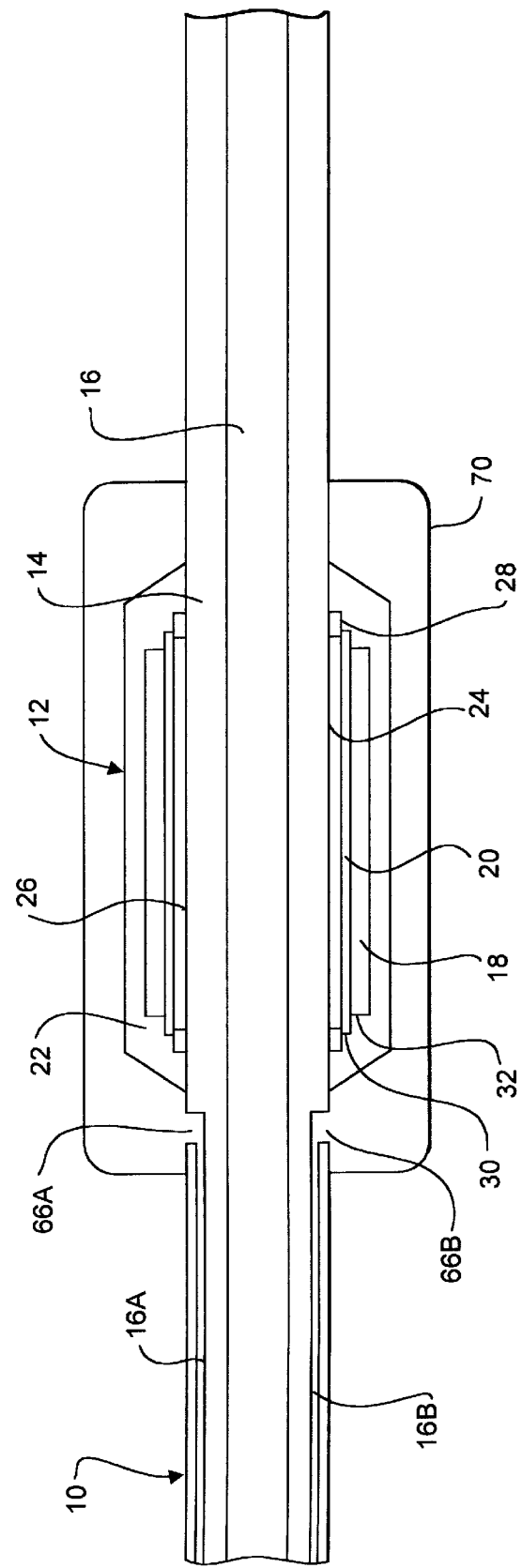
FIG. 5B is a cross section of a catheter with a balloon which include an ultrasound assembly.

The catheter 10 can include a balloon 70 as illustrated in FIG. 5A. The balloon 70 can be constructed from an impermeable material or a permeable membrane or a selectively permeable membrane which allows certain media to flow through the membrane while preventing other media from flowing through the membrane. Suitable membranous materials for the balloon 70 include, but are not limited to cellulose, cellulose acetate, polyvinylchloride, polyolefin, polyurethane and polysulfone. When the balloon 70 is constructed from a permeable membrane or a selectively permeable membrane, the membrane pore sizes are preferably 5 A–2 µm, more preferably 50 A–900 A and most preferably 100 A–300 A in diameter.

As illustrated in FIG. SB, an ultrasound assembly 12, a first media delivery port 66A and a second media delivery port 66B can be positioned within the balloon 70. The first and second media delivery ports 66A, 66B are coupled with a second utility lumen 16A and third utility lumen 16B. The second and third utility lumens 16A, 16B can be coupled with the same media inlet port 68 or with independent media inlet ports 68. When the first and second media delivery ports 66A, 66B are coupled with different media inlet ports 68, different media can be delivered via the second and third media delivery ports 66A, 66B. For instance, a medication media can be delivered via the third utility lumen 16B and an expansion media can be delivered via the second utility lumen 16A. The medication media can include drugs or other medicaments which can provide a therapeutic effect. The expansion media can serve to expand the balloon 70 or wet the membrane comprising the balloon 70. Wetting the membrane comprising the balloon 70 can cause a minimally permeable membrane to become permeable.

Figure 6A:
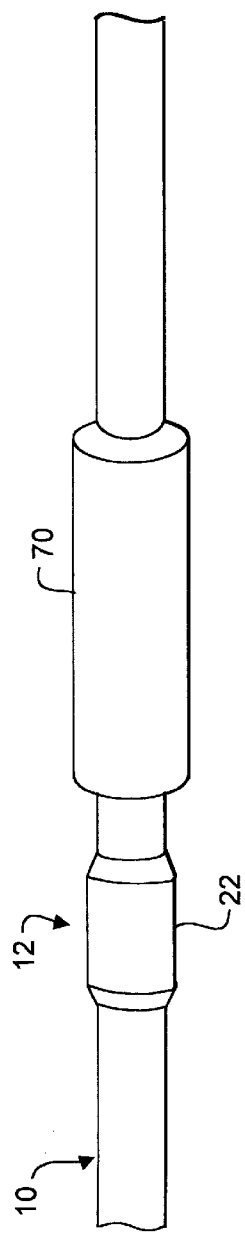
FIG. 6A is a sideview of a catheter with a balloon positioned distally relative to an ultrasound assembly.
Figure 6B:
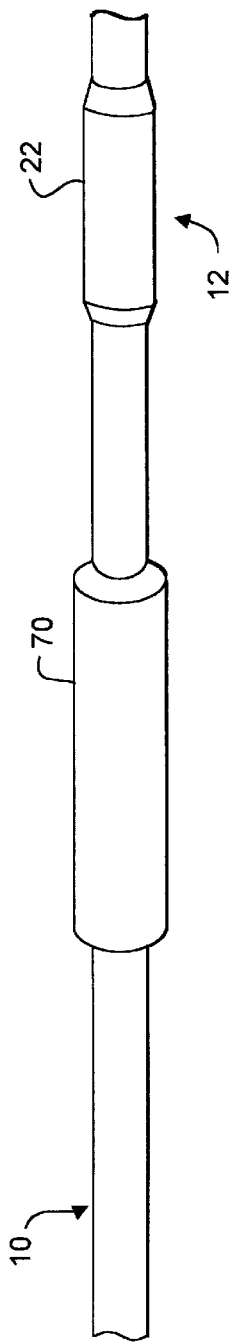
FIG. 6B is a sideview of a catheter with an ultrasound assembly positioned distally relative to a balloon.
Figure 6C:
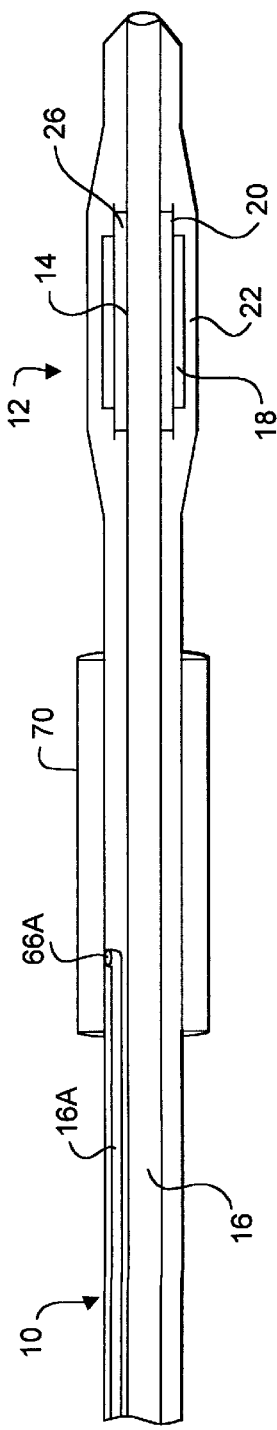
FIG. 6C is a cross section of a catheter with an ultrasound assembly positioned at the distal end of the catheter.

The ultrasound assembly 12 can be positioned outside the balloon 70 as illustrated in FIGS. 6A–6C. In FIG. 6A the balloon 70 is positioned distally of the ultrasound assembly 12 and in FIG. 6B the ultrasound assembly 12 is positioned distally of the balloon 70. FIG. 6C is a cross section a catheter 10 with an ultrasound assembly 12 positioned outside the balloon 70. The catheter includes a second utility lumen 16A coupled with a first media delivery port 66A. The second utility lumen 16A can be used to deliver an expansion media and/or a medication media to the balloon 70. When the balloon 70 is constructed from a permeable membrane, the medication media and/or the expansion media can pass through the balloon 70. Similarly, when the balloon 70 is constructed from a selectively permeable membrane, particular components of the medication media and/or the expansion media can pass through the balloon 70. Pressure can be used to drive the media or components of the media across the balloon 70. Other means such as phoresis can also be used to drive the media or components of the media across the balloon 70.

As illustrated in FIG. 6C, the ultrasound assembly 12 may be positioned at the distal end of the catheter 10. The second utility lumen 16A can be used to deliver an expansion media and/or a medication media to the balloon 70. The utility lumen 16 can be used to deliver a medication media as well as to guide the catheter 10 along a guidewire.

Figure 7A:
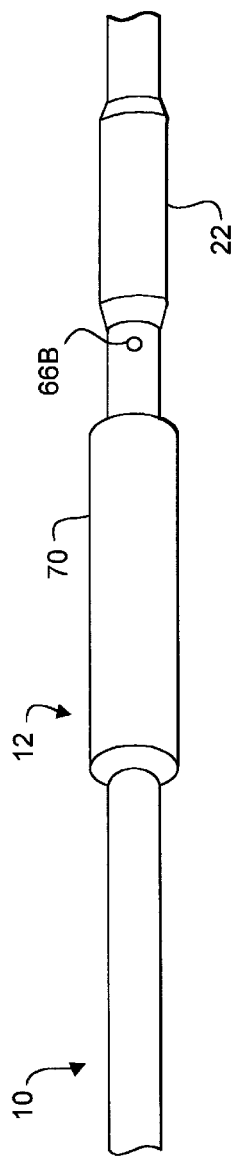
FIG. 7A is a sideview of a catheter with a media delivery port positioned between an ultrasound assembly and a balloon.
Figure 7B:
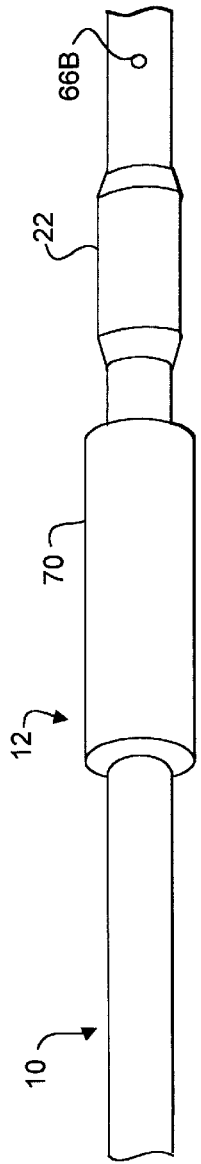
FIG. 7B is a sideview of a catheter with an ultrasound assembly positioned between a media delivery port and a balloon.
Figure 7C:
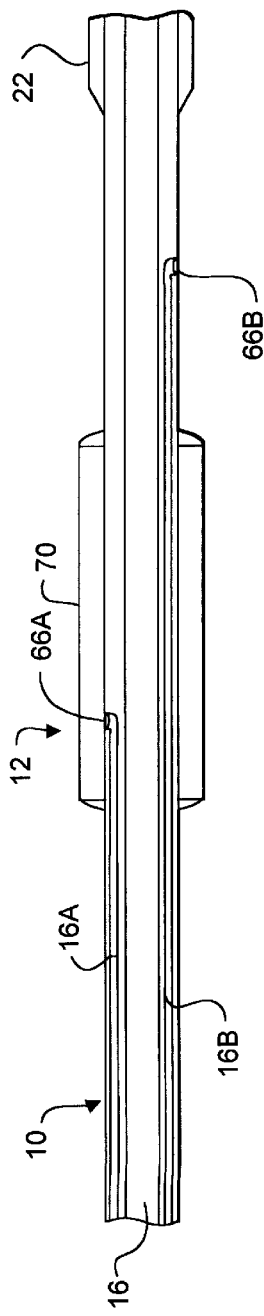
FIG. 7C is a cross section of a catheter with an ultrasound assembly positioned at the distal end of the catheter.

As illustrated in FIGS. 7A–7C, the catheter 10 can include a second media delivery port 66B positioned outside the balloon. In FIGS. 7A–7C the ultrasound assembly 12 and the second media delivery port 66B are positioned distally relative to a balloon 70, however, the balloon 70 can be positioned distally relative to the ultrasound assembly 12 and the second media delivery port 66B. In FIG. 7A the ultrasound assembly 12 is positioned distally of the second media delivery port 66B and in FIG. 7B the second media delivery port 66B is positioned distally of the ultrasound assembly 12.

FIG. 7C is a cross section of the catheter 10 illustrated in FIG. 7A. The catheter 10 includes first and second media delivery ports 66A, 66B coupled with a second utility lumen 16A and third utility lumen 16B. The second and third utility lumens 16A, 16B can be coupled with independent media inlet ports 68 (not shown). The second utility lumen 16A can be used to deliver an expansion media and/or a medication media to the balloon 70 while the third utility lumen 16B can be used to deliver a medication media through the second media delivery port 66B.

Figure 8A:
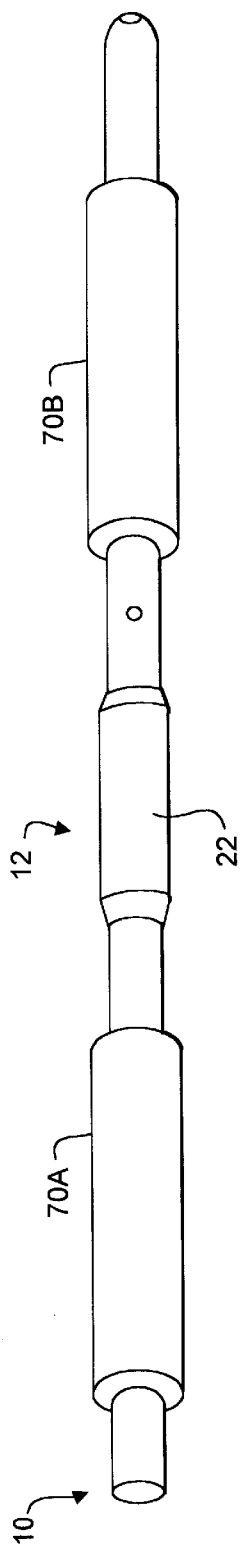
FIG. 8A is a sideview of a catheter including a media delivery port and an ultrasound assembly positioned between first and second balloons.
Figure 8B:
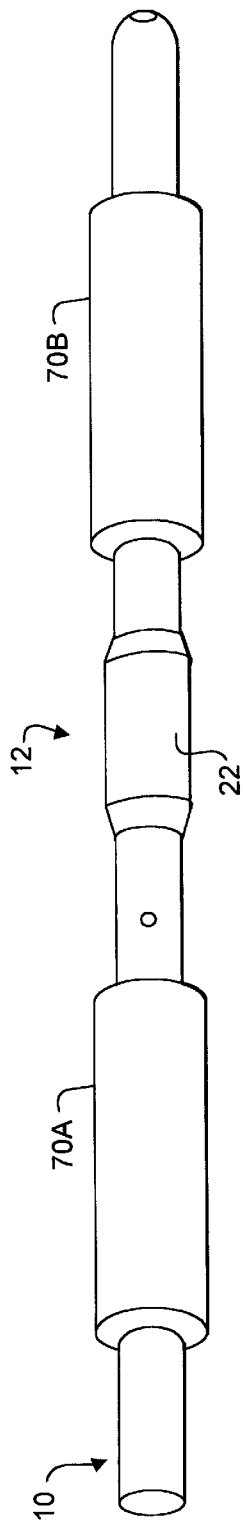
FIG. 8B is a sideview of a catheter including a media delivery port and an ultrasound assembly positioned between first and second balloons.

As illustrated in FIGS. 8A–8B, the catheter 10 can include a first balloon 70A and a second balloon 70B. The ultrasound assembly 12 can be positioned between the first and second balloons 70A, 70B. A second media delivery port 66B can optionally be positioned between the first and second balloons 70A, 70B. In FIG. 8A the second media delivery port 66B is positioned distally relative to the ultrasound assembly and in FIG. 8B the ultrasound assembly is positioned distally relative to the second media delivery port 66B.

Figure 8C:
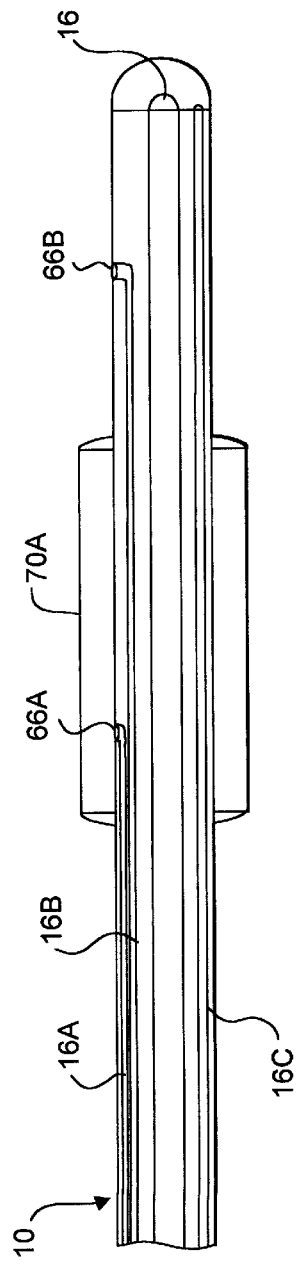
FIG. 8C is a cross section of a balloon included on a catheter having a first and second balloon.

FIG. 8C is a cross section of the first balloon 70A illustrated in FIG. 8B. The catheter includes a second, third and fourth utility lumens 16A, 16B, 16C. The second utility lumen 16A is coupled with a first media delivery port 66A within the first balloon. The third utility lumen 16B is coupled with the second media delivery port 66B and the fourth utility lumen 16C is coupled with a third media delivery port 66C in the second balloon 70B (not shown). The second and fourth utility lumens 16A, 16C can be used to deliver expansion media and/or medication media to the first and second balloon 70A, 70B. The second and fourth utility lumens 16A, 16C can be coupled with the same media inlet port or with independent media inlet ports (not shown). When the second and fourth utility lumens are coupled with the same media inlet port, the pressure within the first and second balloons 70A, 70B will be similar. When the second and fourth utility lumens are coupled with independent media inlet ports, different pressures can be created within the first and second balloons 70A, 70B. The third utility lumen 16B can be coupled with an independent media inlet port and can be used to deliver a medication media via the second media delivery port 66B.

As discussed above, the catheter 10 can include a plurality of ultrasound assemblies. When the catheter 10 includes a plurality of ultrasound assemblies, each ultrasound transducer 18 can each be individually powered. When the elongated body 14 includes N ultrasound transducers 18, the elongated body 14 must include 2N lines to individually power N ultrasound transducers 18. The individual ultrasound transducers 18 can also be electrically coupled in serial or in parallel as illustrated in FIGS. 9A–9B. These arrangements permit maximum flexibility as they require only 2 lines. Each of the ultrasound transducers 18 receive power simultaneously whether the ultrasound transducers 18 are in series or in parallel. When the ultrasound transducers 18 are in series, less current is required to produce the same power from each ultrasound transducer 18 than when the ultrasound transducers 18 are connected in parallel. The reduced current allows smaller lines to be used to provide power to the ultrasound transducers 18 and accordingly increases the flexibility of the elongated body 14. When the ultrasound transducers 18 are connected in parallel, an ultrasound transducer 18 can break down and the remaining ultrasound transducers 18 will continue to operate.

As illustrated in FIG. 9C, a common line 72 can provide power to each ultrasound transducer 18 while each ultrasound transducer 18 has its own return line 74. A particular ultrasound transducer 18 can be individually activated by closing a switch 76 to complete a circuit between the common line 72 and the particular ultrasound transducer's 18 return line 74. Once a switch 76 corresponding to a particular ultrasound transducer 18 has been closed, the amount of power supplied to the ultrasound transducer 18 can be adjusted with the corresponding potentiometer 78. Accordingly, an catheter 10 with N ultrasound transducers 18 requires only N+1 lines and still permits independent control of the ultrasound transducers 18. This reduced number of lines increases the flexibility of the catheter 10. To improve the flexibility of the catheter 10, the individual return lines 74 can have diameters which are smaller than the common line 72 diameter. For instance, in an embodiment where N ultrasound transducers 18 will be powered simultaneously, the diameter of the individual return lines 74 can be the square root of N times smaller than the diameter of the common line 72.

As discussed above, the ultrasound assembly 12 can include at least one temperature sensor 36. Suitable temperature sensors 36 include, but are not limited to, thermistors, thermocouples, resistance temperature detectors (RTD)s, and fiber optic temperature sensors 36 which use thermalchromic liquid crystals. Suitable temperature sensor geometries include, but are not limited to, a point, patch, stripe and a band encircling the ultrasound transducer 18.

Figure 10:
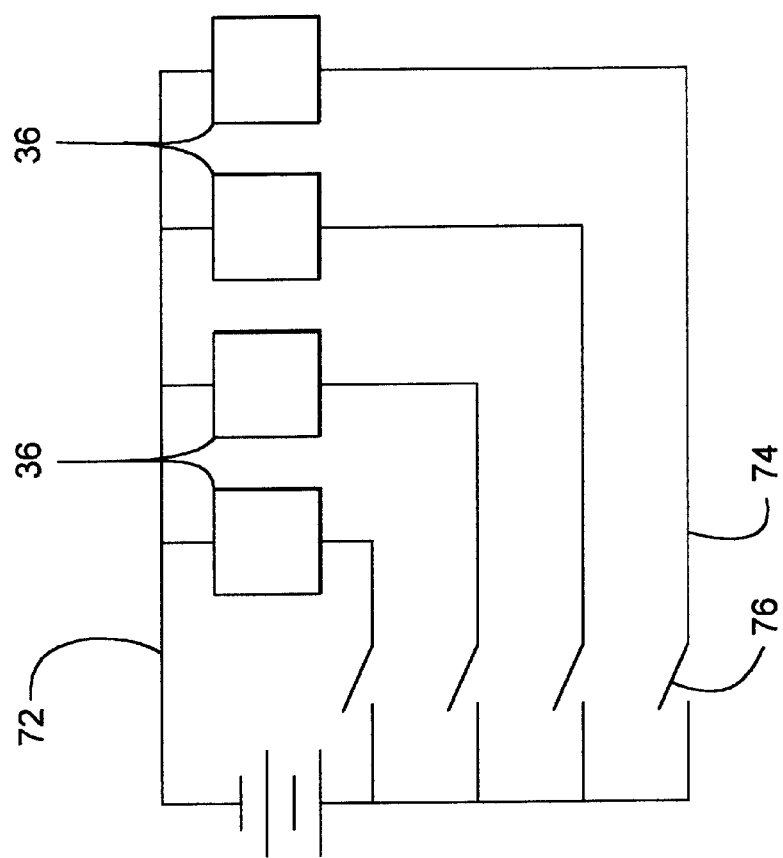
FIG. 10 illustrates a circuit for electrically coupling temperature sensors.

When the ultrasound assembly 12 includes a plurality of temperature sensors 36, the temperature sensors 36 can be electrically connected as illustrated in FIG. 10. Each temperature sensor 36 can be coupled with a common line 72 and then include its own return line 74. Accordingly, N+1 lines can be used to independently sense the temperature at the temperature sensors 36 when N temperature sensors 36 are employed. A suitable common line 72 can be constructed from Constantine and suitable return lines 74 can be constructed from copper. The temperature at a particular temperature sensor 36 can be determined by closing a switch 76 to complete a circuit between the thermocouple's return line 74 and the common line 72. When the temperature sensors 36 are thermocouples, the temperature can be calculated from the voltage in the circuit. To improve the flexibility of the catheter 10, the individual return lines 74 can have diameters which are smaller than the common line 72 diameter.

Each temperature sensor 36 can also be independently electrically coupled. Employing N independently electrically coupled temperature sensors 36 requires 2N lines to pass the length of the catheter 10.

The catheter 10 flexibility can also be improved by using fiber optic based temperature sensors 36. The flexibility can be improved because only N fiber optics need to be employed sense the temperature at N temperature sensors 36.

Figure 11:
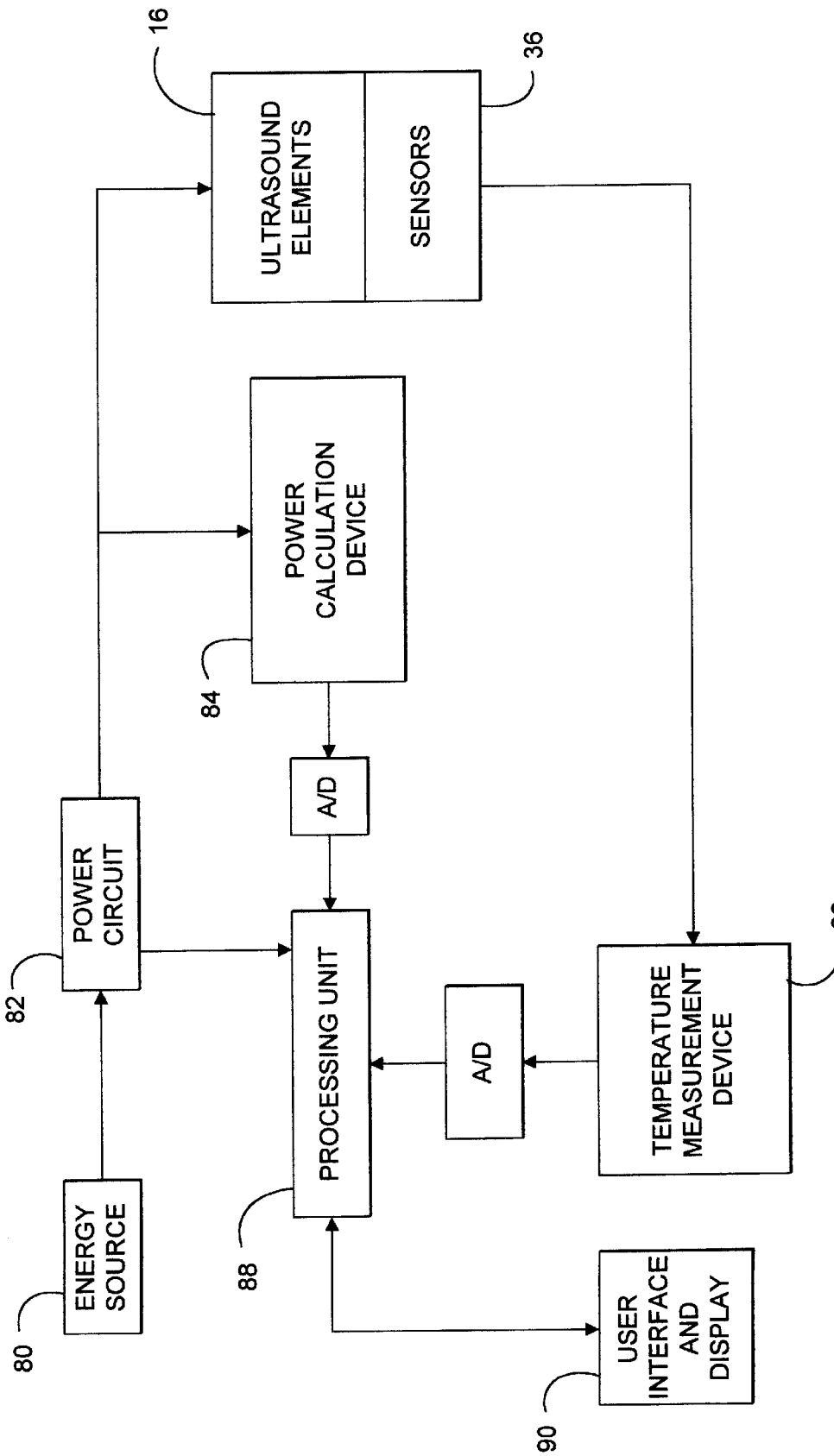
FIG. 11 illustrates a feedback control system for use with a catheter including an ultrasound assembly.

The catheter 10 can be coupled with a feedback control system as illustrated in FIG. 11. The temperature at each temperature sensor 36 is monitored and the output power of an energy source adjusted accordingly. The physician can, if desired, override the closed or open loop system.

The feedback control system includes an energy source 80, power circuits 82 and a power calculation device 84 coupled with each ultrasound transducer 18. A temperature measurement device 86 is coupled with the temperature sensors 36 on the catheter 10. A processing unit 88 is coupled with the power calculation device 84, the power circuits 82 and a user interface and display 90.

In operation, the temperature at each temperature sensor 36 is determined at the temperature measurement device 86. The processing unit 88 receives a signals indicating the determined temperatures from the temperature measurement device 86. The determined temperatures can then be displayed to the user at the user interface and display 90.

The processing unit 88 includes logic for generating a temperature control signal. The temperature control signal is proportional to the difference between the measured temperature and a desired temperature. The desired temperature can be determined by the user. The user can set the predetermined temperature at the user interface and display 90.

The temperature control signal is received by the power circuits 82. The power circuits 82 adjust the power level of the energy supplied to the ultrasound transducers 18 from the energy source 80. For instance, when the temperature control signal is above a particular level, the power supplied to a particular ultrasound transducer 18 is reduced in proportion to the magnitude of the temperature control signal. Similarly, when the temperature control signal is below a particular level, the power supplied to a particular ultrasound transducer 18 is increased in proportion to the magnitude of the temperature control signal. After each power adjustment, the processing unit 88 monitors the temperature sensors 36 and produces another temperature control signal which is received by the power circuits 82.

The processing unit 88 can also include safety control logic. The safety control logic detects when the temperature at a temperature sensor 36 has exceeded a safety threshold. The processing unit 88 can then provide a temperature control signal which causes the power circuits 82 to stop the delivery of energy from the energy source 80 to the ultrasound transducers 18.

The processing unit 88 also receives a power signal from the power calculation device 84. The power signal can be used to determine the power being received by each ultrasound transducer 18. The determined power can then be displayed to the user on the user interface and display 90.

The feedback control system can maintain the tissue adjacent to the ultrasound transducers 18 within a desired temperature range for a selected period of time. As described above, the ultrasound transducers 18 can be electrically connected so each ultrasound transducer 18 can generate an independent output. The output maintains a selected energy at each ultrasound transducer 18 for a selected length of time.

The processing unit 88 can be a digital or analog controller, or a computer with software. When the processing unit 88 is a computer it can include a CPU coupled through a system bus. The user interface and display 90 can be a mouse, keyboard, a disk drive, or other non-volatile memory systems, a display monitor, and other peripherals, as are known in the art. Also coupled to the bus is a program memory and a data memory.

In lieu of the series of power adjustments described above, a profile of the power delivered to each ultrasound transducer 18 can be incorporated in the processing unit 88 and a preset amount of energy to be delivered may also be profiled. The power delivered to each ultrasound transducer 18 can the be adjusted according to the profiles.

Figure 12C:
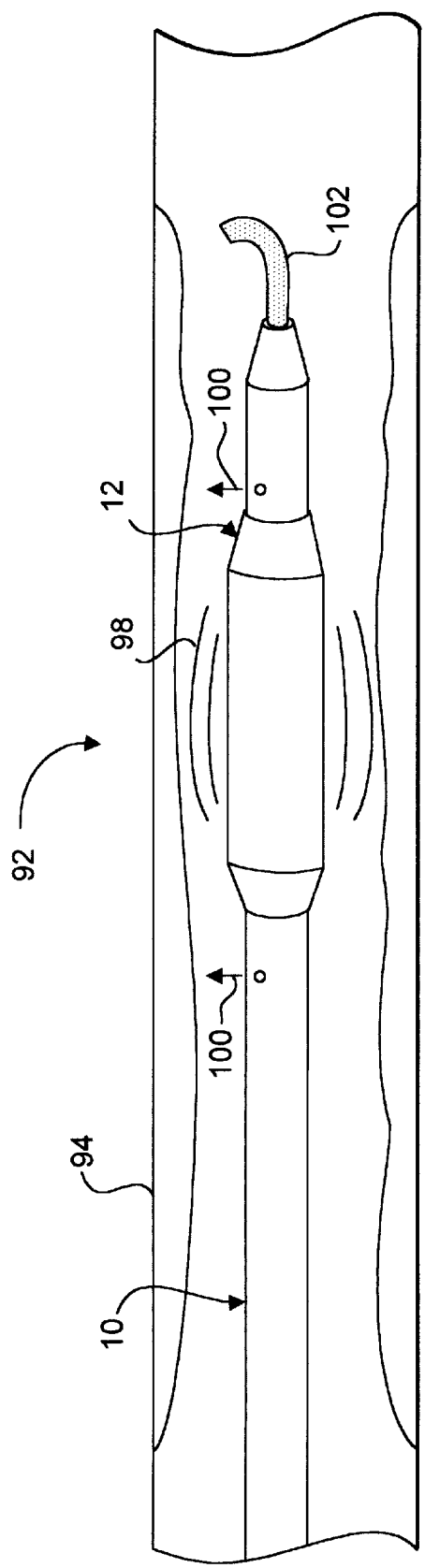
FIG. 12C illustrates an ultrasound assembly positioned adjacent a treatment site and a media is delivered via a media delivery port while a guidewire is positioned in a utility lumen.

FIGS. 12A–12C illustrate operation of various embodiments of catheters 10 which include ultrasound assemblies according to the present invention. In FIG. 12A, the catheter 10 is positioned so the ultrasound assembly 12 is adjacent to a treatment site 92 within a vessel 94. Suitable treatment sites 92 include, but are not limited to, thrombi in veins and other abnormalities of vessel within the body. The catheter 10 can be guided to the treatment site 92 by positioning a guidewire in the utility lumen 16 and applying conventional over-the-guidewire techniques. When the catheter 10 is in position, the guidewire is removed from the utility lumen 16 and media can be delivered via the utility lumen 16 as illustrated by the arrows 100. In FIG. 12A, microbubbles 96 are delivered to the treatment site 92 via the utility lumen 16 and ultrasound energy 98 is delivered from the ultrasound transducer 18. The delivery of ultrasound energy 98 can be before, after, during or intermittently with the delivery of the microbubbles 96. Because the transmission of ultrasound energy 98 into the utility lumen 16 is reduced, the microbubbles 96 are not burst within the utility lumen 16 but burst when they are exposed to ultrasound energy 98 outside the catheter 10.

In FIG. 12B, ultrasound energy 98 is delivered from the ultrasound transducer 18 and a media is delivered through the media delivery port 66 as illustrated by the arrows 100. The delivery of ultrasound energy 98 can be before, after, during or intermittently with the delivery of the media via the media delivery port 66. As illustrated in FIG. 12C, the guidewire 102 can remain in the utility lumen 16 during the delivery of the media via the media delivery ports 66. Because the transmission of ultrasound energy 98 into the utility lumen 16 is reduced, the change in the frequency of the ultrasound transducer 18 which is due to the presence of the guidewire in the utility lumen 16 is also reduced.

In FIG. 12D, a catheter 10 including a balloon 70 is positioned with the balloon adjacent the treatment site 92. In FIG. 12E, the balloon 70 is expanded into contact with the treatment site 92. When the balloon 70 is constructed from a membrane or a selectively permeable membrane a media can be delivered to the treatment site 92 via the balloon 70. The media can serve to wet the membrane or can include a drug or other medicament which provides a therapeutic effect. Ultrasound energy 98 can be delivered from the ultrasound assembly 12 before, after, during or intermittently with the delivery of the media. The ultrasound energy 98 can serve to drive the media across the membrane via phonophoresis or can enhance the therapeutic effect of the media.

Figure 12F:
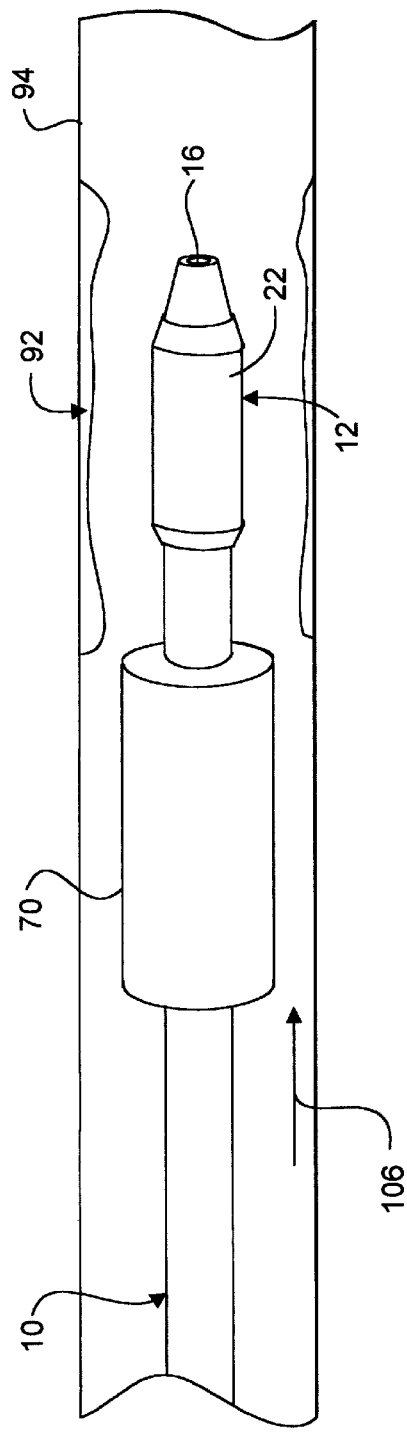
FIG. 12F illustrates a catheter with an ultrasound assembly outside a balloon positioned at a treatment site.
Figure 12G:
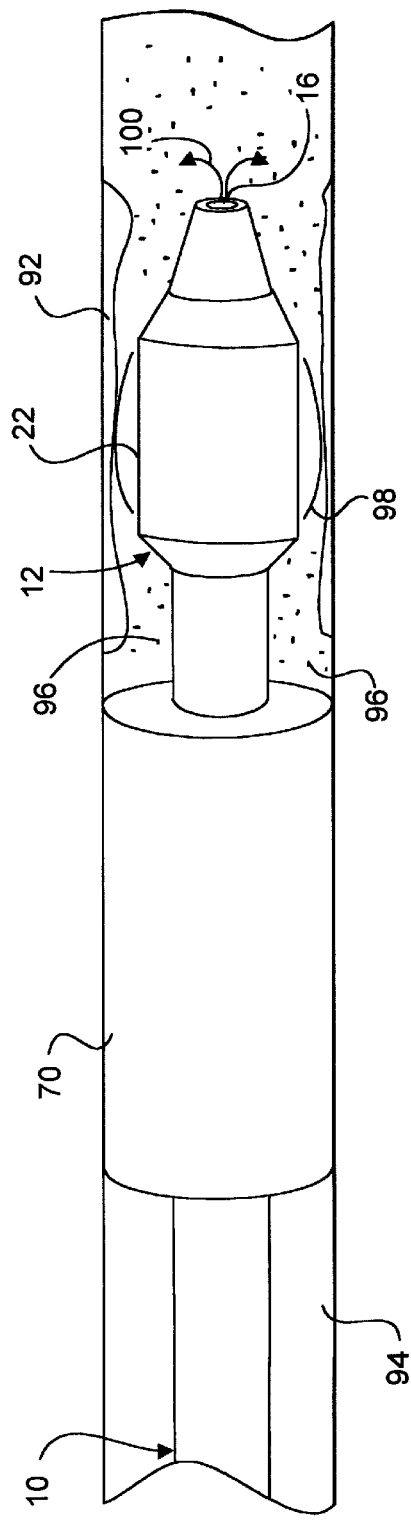
FIG. 12G illustrates the balloon of FIG. 12F expanded into contact with a vessel so as to occlude the vessel.

In FIG. 12F a catheter 10 with an ultrasound assembly 12 outside a balloon 70 is positioned at the treatment site 92 so the ultrasound assembly 12 is adjacent the treatment site 92. A fluid within the vessel flows past the balloon as indicated by the arrow 106. In FIG. 12G, the balloon 70 is expanded into contact with the vessel 94. The balloon 70 can be constructed from an impermeable material so the vessel 94 is occluded. As a result, the fluid flow through the vessel 94 is reduced or stopped. A medication media is delivered through the utility lumen 16 and ultrasound energy 98 is delivered from the ultrasound assembly 12. In embodiments of the catheter 10 including a media delivery port 66 outside of the balloon 70 (i.e. FIGS. 7A–7C), the medication media can be delivered via the media delivery port 66. Further, a first medication media can be delivered via the media delivery port 66 while a second medication media can be delivered via the utility lumen 16 or while a guidewire is positioned within the utility lumen 16. The ultrasound energy 98 can be delivered from the ultrasound assembly 12 before, after, during or intermittently with the delivery of the media. The occlusion of the vessel 94 before the delivery of the media can serve to prevent the media from being swept from the treatment site 92 by the fluid flow. Although the balloon 70 illustrated in FIGS. 12F–12G is positioned proximally relative to the ultrasound assembly 12, the fluid flow through the vessel 94 can also be reduced by expanding a single balloon 70 which is positioned distally relative to the ultrasound assembly 12.

Figure 12H:
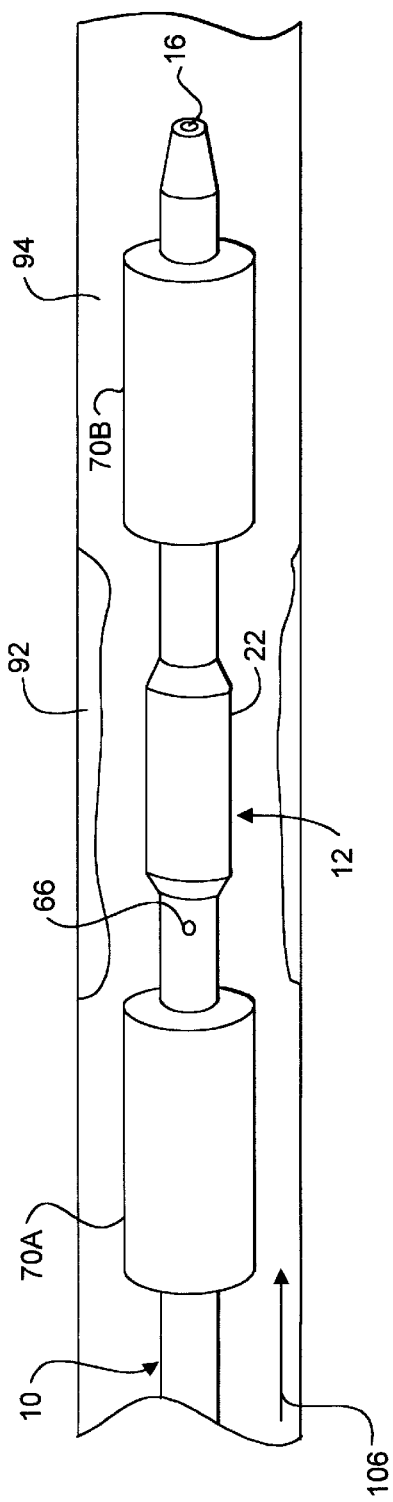
FIG. 12H illustrates a catheter with an ultrasound assembly outside a first and second balloon positioned at a treatment site.
Figure 12I:
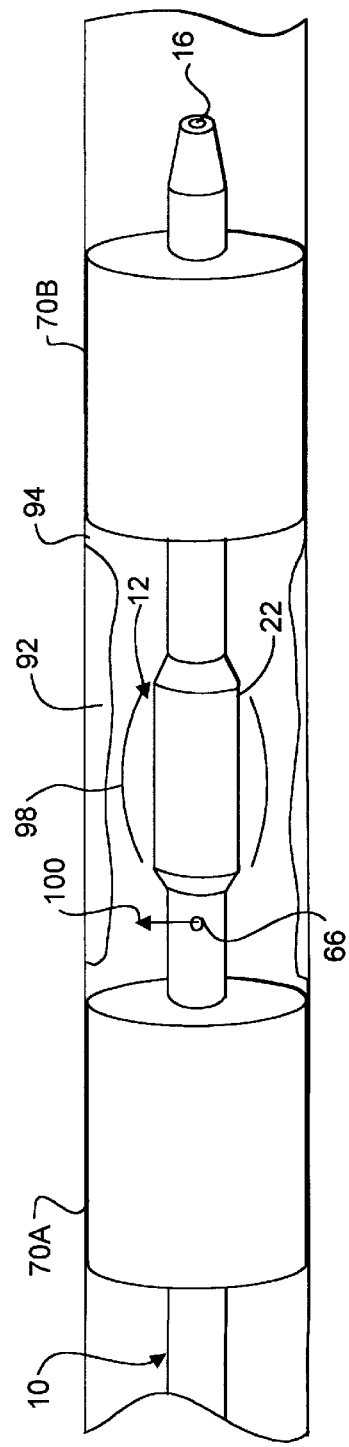
FIG. 12I illustrates the first and second balloon of FIG. 12H expanded into contact with a vessel so as to occlude the vessel.

In FIG. 12H a catheter 10 including a first balloon 70A and a second balloon 70B is positioned at a treatment site 92 so the ultrasound assembly 12 is positioned adjacent the treatment site 92. A fluid within the vessel 94 flows past the balloon 70 as indicated by the arrow 106. In FIG. 12I, the first and second balloons 70A, 70B are expanded into contact with the vessel 94. The first and second balloons 70A, 70B can be constructed from an impermeable material so the vessel 94 is occluded proximally and distally of the ultrasound assembly 12. As a result, the fluid flow adjacent the treatment site 92 is reduced or stopped. A medication media is delivered through the media delivery port 66 and ultrasound energy 98 is delivered from the ultrasound assembly 12. The ultrasound energy 98 can be delivered from the ultrasound assembly 12 before, after, during or intermittently with the delivery of the media. The occlusion of the vessel 94 before the delivery of the media can serve to prevent the media from being swept from the treatment site 92 by the fluid flow.

The catheters disclosed above can include radiopaque markers to aid in positioning the catheter relative to the treatment site 92.

The foregoing description of a preferred embodiment of the invention has been presented for purposes of illustration and description. It is not intended to be exhaustive or to limit the invention to the precise forms disclosed. Obviously, many modifications, combinations and variations will be apparent to practitioners skilled in this art.

What is claimed is:

1. A catheter, comprising:

an elongated body with an exterior surface;

an ultrasound transducer with a longitudinal length; and a support member supporting the ultrasound transducer at the exterior surface of the elongated body, the support member at least partially defining a chamber adjacent to the exterior surface of the elongated body, the chamber reducing transmission of ultrasound energy from the ultrasound transducer into the elongated body along the longitudinal length of the ultrasound transducer; and a support positioned between the support member and the elongated body.

2. The catheter of claim 1, further comprising:

a coating adjacent an external surface of the ultrasound transducer; and at least one temperature sensor coupled with the coating.

3. The catheter of claim 2, wherein the at least one temperature sensor is positioned within the coating.

4. The catheter of claim 1, further comprising:

a support positioned between the support member and the elongated body.

5. The catheter of claim 4, wherein the support is integral with the support member.

6. The catheter of claim 1, wherein the chamber is filled with a low acoustic impedance material.

7. The catheter of claim 1, wherein the chamber is air filled.

8. The catheter of claim 1, wherein the chamber is filled with nitrogen.

9. The catheter of claim 1, wherein the chamber is evacuated.

10. The catheter of claim 1, further comprising:

at least one temperature sensor; and a feedback control system for adjusting a power delivered to the ultrasound transducer in response to a signal from the at least one temperature sensor.

11. The catheter of claim 1, further comprising:

a coating adjacent the ultrasound transducer and supporting the support member.

12. The catheter of claim 1, further comprising:
at least one utility lumen extending through the elongated body.

13. The catheter of claim 1, wherein the ultrasound transducer includes ends and the chamber extends beyond the ends of the ultrasound transducer.

14. A catheter, comprising:
an elongated body with an exterior surface;
an ultrasound transducer; and
a support member supporting the ultrasound transducer in a spaced apart relationship from the exterior surface of the elongated body such that a chamber is formed between the support member and the exterior surface of the elongated body, wherein the chamber is filled with a low acoustic impedance material.

15. The catheter of claim 14, further comprising:
a coating adjacent an external surface of the ultrasound transducer; and
at least one temperature sensor coupled with the coating.

16. The catheter of claim 15, wherein the at least one temperature sensor is positioned within the coating.

17. The catheter of claim 14, further comprising:
a support positioned between the support member and the elongated body.

18. The catheter of claim 17, wherein the support is integral with the support member.

19. The catheter of claim 14, wherein the chamber is air filled.

20. The catheter of claim 14, wherein the chamber is filled with nitrogen.

21. The catheter of claim 14, wherein the chamber is evacuated.

22. The catheter of claim 14, further comprising:
at least one temperature sensor; and
a feedback control system for adjusting a power delivered to the ultrasound transducer in response to a signal from the at least one temperature sensor.

23. The catheter of claim 14, further comprising:
a coating adjacent the ultrasound transducer and supporting the support member.

24. The catheter of claim 14, further comprising:
at least one utility lumen extending through the elongated body.

25. The catheter of claim 14, wherein the ultrasound transducer includes a proximal end and a distal end and the chamber extends beyond the proximal and distal ends of the ultrasound transducer.

26. The catheter of claim 14, wherein the support member surrounds the elongated body.

27. The catheter of claim 14, wherein the support member is adjacent to an internal side of the ultrasound transducer.

28. The catheter of claim 14, wherein the support member is positioned between the ultrasound transducer and the elongated body.

29. A catheter, comprising:
an elongated body with an exterior surface;
an ultrasound transducer;
a support member supporting the ultrasound transducer at the exterior surface of the elongated body, the support member defining a chamber adjacent to an exterior surface of the elongated body, the chamber reducing transmission of ultrasound energy from the ultrasound transducer into the elongated body along the longitudinal length of the ultrasound transducer;
a coating adjacent an external surface of the ultrasound transducer; and
at least one temperature sensor within the coating.

30. The catheter of claim 29, further comprising:
a support positioned between the support member and the elongated body.

31. The catheter of claim 30, wherein the support is integral with the support member.

32. The catheter of claim 29, wherein the chamber is filled with a low acoustic impedance material.

33. The catheter of claim 29, wherein the chamber is air filled.

34. The catheter of claim 29, wherein the chamber is filled with nitrogen.

35. The catheter of claim 29, wherein the chamber is evacuated.

36. The catheter of claim 29, wherein the coating includes parylene.

37. The catheter of claim 29, further comprising:
at least one temperature sensor; and
a feedback control system for adjusting a power delivered to the ultrasound transducer in response to a signal from the at least one temperature sensor.

38. The catheter of claim 29, further comprising:
a coating supporting the support member.

39. The catheter of claim 29, further comprising:
at least one utility lumen extending through the ultrasound transducer.

40. The catheter of claim 29, wherein the ultrasound transducer includes ends and the chamber extends beyond the ends of the ultrasound transducer.

* * * * *